United States Patent
Dibenedetto et al.

(10) Patent No.: US 9,710,711 B2
(45) Date of Patent: Jul. 18, 2017

(54) ATHLETIC ACTIVITY HEADS UP DISPLAY SYSTEMS AND METHODS

(71) Applicant: adidas AG, Herzogenaurach (DE)

(72) Inventors: Christian Dibenedetto, Portland, OR (US); Jon H. Werner, Austin, TX (US); Scott Tomlinson, Portland, OR (US); Aurel Coza, Portland, OR (US); Ben Valenti, Portland, OR (US); Katrina Lee, Portland, OR (US); Alan Lee, Montara, CA (US); Amy Jones Vaterlaus, Portland, OR (US)

(73) Assignee: adidas AG, Herzogenaurach (DE)

( * ) Notice: Subject to any disclaimer, the term of this patent is extended or adjusted under 35 U.S.C. 154(b) by 204 days.

(21) Appl. No.: 14/316,425

(22) Filed: Jun. 26, 2014

(65) Prior Publication Data

US 2015/0379351 A1    Dec. 31, 2015

(51) Int. Cl.
| | |
|---|---|
| *G06K 9/00* | (2006.01) |
| *G02B 27/01* | (2006.01) |
| *G06T 19/00* | (2011.01) |
| *A61B 5/00* | (2006.01) |
| *G09B 19/00* | (2006.01) |
| *A61B 5/11* | (2006.01) |

(52) U.S. Cl.
CPC ......... *G06K 9/00671* (2013.01); *A61B 5/486* (2013.01); *G02B 27/017* (2013.01); *G02B 27/0189* (2013.01); *G06T 19/006* (2013.01); *G09B 19/0038* (2013.01); *A61B 5/1118* (2013.01); *A61B 5/6803* (2013.01); *A61B 5/742* (2013.01); *A61B 2503/10* (2013.01); *G02B 2027/0178* (2013.01); *G02B 2027/0187* (2013.01)

(58) Field of Classification Search
None
See application file for complete search history.

(56) References Cited

U.S. PATENT DOCUMENTS

| | | | |
|---|---|---|---|
| 4,202,350 A | 5/1980 | Walton | |
| 4,312,358 A | 1/1982 | Barney | |

(Continued)

FOREIGN PATENT DOCUMENTS

| | | |
|---|---|---|
| CN | 101224337 A | 7/2008 |
| CN | 101701823 A | 5/2010 |

(Continued)

OTHER PUBLICATIONS

Deltatre-Vizrt ("Deltatre and Vizrt expanding partnership for Magma Pro Football solution", 2013, http://www.vizrt.com/news/newsgrid/39609/deltatre_and_Vizrt_expanding_partnership_for_Magma_Pro_Football_solution).*

(Continued)

*Primary Examiner* — Kee M Tung
*Assistant Examiner* — Xin Sheng
(74) *Attorney, Agent, or Firm* — Sterne, Kessler, Goldstein & Fox P.L.L.C.

(57) ABSTRACT

A method of using an athletic activity heads up display system during an athletic activity includes the steps of a heads up display unit receiving information about a sport ball and the heads up display unit displaying an image to an individual based on the information, where the image is overlaid on the individual's present field of view of an environment.

9 Claims, 20 Drawing Sheets

(56) References Cited

U.S. PATENT DOCUMENTS

| | | |
|---|---|---|
| 4,572,197 A | 2/1986 | Moore et al. |
| 4,580,572 A | 4/1986 | Granek et al. |
| 4,889,131 A | 12/1989 | Salem et al. |
| 4,909,260 A | 3/1990 | Salem et al. |
| 4,962,469 A | 10/1990 | Ono et al. |
| 5,007,427 A | 4/1991 | Suzuki et al. |
| 5,111,818 A | 5/1992 | Suzuki et al. |
| 5,148,002 A | 9/1992 | Kuo et al. |
| 5,153,584 A | 10/1992 | Engira |
| 5,204,670 A | 4/1993 | Stinton |
| 5,210,540 A | 5/1993 | Masumoto |
| 5,353,793 A | 10/1994 | Bornn |
| 5,400,254 A | 3/1995 | Fujita |
| 5,583,776 A | 12/1996 | Levi et al. |
| 5,592,401 A | 1/1997 | Kramer |
| 5,611,085 A | 3/1997 | Rasmussen |
| 5,724,025 A | 3/1998 | Tavori |
| 5,724,265 A | 3/1998 | Hutchings |
| 5,769,755 A | 6/1998 | Henry et al. |
| 5,802,492 A | 9/1998 | DeLorme et al. |
| 5,825,327 A | 10/1998 | Krasner |
| 5,899,963 A | 5/1999 | Hutchings |
| 5,947,868 A | 9/1999 | Dugan |
| 5,948,040 A | 9/1999 | DeLorme et al. |
| 5,955,667 A | 9/1999 | Fyfe |
| 5,976,083 A | 11/1999 | Richardson et al. |
| 5,989,157 A | 11/1999 | Walton |
| 6,002,982 A | 12/1999 | Fry |
| 6,013,007 A | 1/2000 | Root et al. |
| 6,032,108 A | 2/2000 | Seiple et al. |
| 6,047,203 A | 4/2000 | Sackner et al. |
| 6,066,093 A | 5/2000 | Kelly et al. |
| 6,073,086 A | 6/2000 | Marinelli |
| 6,097,345 A | 8/2000 | Walton |
| 6,122,340 A | 9/2000 | Darley et al. |
| 6,135,951 A | 10/2000 | Richardson et al. |
| 6,145,389 A | 11/2000 | Ebeling et al. |
| 6,148,262 A | 11/2000 | Fry |
| 6,148,271 A | 11/2000 | Marinelli |
| 6,151,563 A | 11/2000 | Marinelli |
| 6,157,898 A | 12/2000 | Marinelli |
| 6,198,394 B1 | 3/2001 | Jacobsen et al. |
| 6,204,807 B1 | 3/2001 | Odagiri et al. |
| 6,246,362 B1 | 6/2001 | Tsubata et al. |
| 6,254,492 B1 * | 7/2001 | Taggett .............. A63B 24/0003 434/252 |
| 6,254,551 B1 | 7/2001 | Varis |
| 6,266,623 B1 | 7/2001 | Vock et al. |
| 6,298,314 B1 | 10/2001 | Blackadar et al. |
| 6,301,964 B1 | 10/2001 | Fyfe et al. |
| 6,305,221 B1 | 10/2001 | Hutchings |
| 6,336,365 B1 | 1/2002 | Blackadar et al. |
| 6,356,856 B1 | 3/2002 | Damen et al. |
| 6,357,147 B1 | 3/2002 | Darley et al. |
| 6,381,482 B1 | 4/2002 | Jayaraman et al. |
| 6,443,890 B1 | 9/2002 | Schulze |
| 6,463,385 B1 | 10/2002 | Fry |
| 6,478,736 B1 | 11/2002 | Mault |
| 6,493,652 B1 | 12/2002 | Ohlenbusch et al. |
| 6,513,381 B2 | 2/2003 | Fyfe et al. |
| 6,513,532 B2 | 2/2003 | Mault et al. |
| 6,536,139 B2 | 3/2003 | Darley et al. |
| 6,551,252 B2 | 4/2003 | Sackner et al. |
| 6,582,330 B1 | 6/2003 | Rehkemper et al. |
| 6,585,622 B1 | 7/2003 | Shum et al. |
| 6,590,536 B1 | 7/2003 | Walton |
| 6,611,789 B1 | 8/2003 | Darley |
| 6,616,613 B1 | 9/2003 | Goodman |
| 6,626,799 B2 | 9/2003 | Watterson et al. |
| 6,716,139 B1 | 4/2004 | Hosseinzadeh-Dolkhani et al. |
| 6,736,759 B1 | 5/2004 | Stubbs et al. |
| 6,745,069 B2 | 6/2004 | Nissila et al. |
| 6,790,178 B1 | 9/2004 | Mault et al. |
| 6,798,378 B1 | 9/2004 | Walters |
| 6,832,109 B2 | 12/2004 | Nissila |
| 6,876,947 B1 | 4/2005 | Darley et al. |
| 6,882,955 B1 | 4/2005 | Ohlenbusch et al. |
| 6,885,971 B2 | 4/2005 | Vock et al. |
| 6,898,550 B1 | 5/2005 | Blackadar et al. |
| 6,959,259 B2 | 10/2005 | Vock et al. |
| 6,970,731 B1 | 11/2005 | Jayaraman et al. |
| 7,062,225 B2 | 6/2006 | White |
| 7,072,789 B2 | 7/2006 | Vock et al. |
| 7,092,846 B2 | 8/2006 | Vock et al. |
| 7,171,331 B2 | 1/2007 | Vock et al. |
| 7,187,924 B2 | 3/2007 | Ohlenbusch et al. |
| 7,200,517 B2 | 4/2007 | Darley et al. |
| 7,220,220 B2 | 5/2007 | Stubbs et al. |
| 7,251,454 B2 | 7/2007 | White |
| 7,254,516 B2 | 8/2007 | Case, Jr. et al. |
| 7,273,431 B2 | 9/2007 | DeVall |
| 7,292,867 B2 | 11/2007 | Werner et al. |
| 7,428,472 B2 | 9/2008 | Darley et al. |
| 7,457,724 B2 | 11/2008 | Vock et al. |
| 7,467,060 B2 | 12/2008 | Kulach et al. |
| 7,480,512 B2 | 1/2009 | Graham et al. |
| 7,552,031 B2 | 6/2009 | Vock et al. |
| 7,559,902 B2 | 7/2009 | Ting et al. |
| 7,647,196 B2 | 1/2010 | Kahn et al. |
| 7,650,257 B2 | 1/2010 | Alexander et al. |
| 7,670,263 B2 | 3/2010 | Ellis et al. |
| 7,670,295 B2 | 3/2010 | Sackner et al. |
| 7,680,523 B2 | 3/2010 | Rytky |
| 7,689,378 B2 | 3/2010 | Kolen |
| 7,698,830 B2 | 4/2010 | Townsend et al. |
| 7,706,815 B2 | 4/2010 | Graham et al. |
| 7,715,982 B2 | 5/2010 | Grenfell et al. |
| 7,805,149 B2 | 9/2010 | Werner et al. |
| 7,805,150 B2 | 9/2010 | Graham et al. |
| 7,844,415 B1 | 11/2010 | Bryant et al. |
| 7,890,291 B2 | 2/2011 | Godin et al. |
| 7,891,666 B2 | 2/2011 | Kuenzler et al. |
| 7,980,998 B2 | 7/2011 | Shemesh et al. |
| 8,060,337 B2 | 11/2011 | Kulach et al. |
| 8,253,586 B1 | 8/2012 | Matak |
| 8,540,560 B2 | 9/2013 | Crowley et al. |
| 8,579,632 B2 | 11/2013 | Crowley |
| 8,818,478 B2 | 8/2014 | Scheffler et al. |
| 9,141,759 B2 | 9/2015 | Burich et al. |
| 9,257,054 B2 | 2/2016 | Coza et al. |
| 9,317,660 B2 | 4/2016 | Burich et al. |
| 9,392,941 B2 | 7/2016 | Powch et al. |
| 2002/0032386 A1 | 3/2002 | Sackner et al. |
| 2002/0068873 A1 | 6/2002 | Nissila |
| 2002/0107433 A1 | 8/2002 | Mault |
| 2002/0160883 A1 | 10/2002 | Dugan |
| 2003/0163287 A1 | 8/2003 | Vock et al. |
| 2003/0208409 A1 | 11/2003 | Mault |
| 2003/0224337 A1 | 12/2003 | Shum et al. |
| 2004/0046692 A1 | 3/2004 | Robson et al. |
| 2004/0102931 A1 | 5/2004 | Ellis et al. |
| 2004/0171956 A1 | 9/2004 | Babashan |
| 2004/0177531 A1 | 9/2004 | DiBenedetto et al. |
| 2004/0199056 A1 | 10/2004 | Husemann et al. |
| 2004/0209600 A1 | 10/2004 | Werner et al. |
| 2005/0010096 A1 | 1/2005 | Blackadar |
| 2005/0054941 A1 | 3/2005 | Ting et al. |
| 2005/0195094 A1 | 9/2005 | White |
| 2005/0197063 A1 | 9/2005 | White |
| 2005/0227811 A1 | 10/2005 | Shum et al. |
| 2005/0233815 A1 | 10/2005 | McCreary et al. |
| 2005/0250458 A1 | 11/2005 | Graham et al. |
| 2005/0266961 A1 | 12/2005 | Shum et al. |
| 2006/0020421 A1 | 1/2006 | Darley et al. |
| 2006/0025282 A1 | 2/2006 | Redmann |
| 2006/0135297 A1 | 6/2006 | Cruciani |
| 2006/0136173 A1 | 6/2006 | Case, Jr. et al. |
| 2006/0148594 A1 | 7/2006 | Saintoyant et al. |
| 2006/0189360 A1 | 8/2006 | White |
| 2006/0240865 A1 | 10/2006 | White |
| 2006/0246869 A1 | 11/2006 | Ohlenbusch et al. |
| 2007/0006489 A1 | 1/2007 | Case, Jr. et al. |
| 2007/0011919 A1 | 1/2007 | Case, Jr. |
| 2007/0021269 A1 | 1/2007 | Shum |

(56) References Cited

U.S. PATENT DOCUMENTS

| | | | |
|---|---|---|---|
| 2007/0032318 A1 | 2/2007 | Nishimura et al. | |
| 2007/0059675 A1 | 3/2007 | Kuenzler et al. | |
| 2007/0060425 A1 | 3/2007 | Kuenzler et al. | |
| 2007/0061105 A1 | 3/2007 | Darley et al. | |
| 2007/0191083 A1 | 8/2007 | Kuenzler et al. | |
| 2007/0203665 A1 | 8/2007 | Darley et al. | |
| 2007/0208531 A1 | 9/2007 | Darley et al. | |
| 2007/0247306 A1 | 10/2007 | Case | |
| 2007/0287596 A1 | 12/2007 | Case et al. | |
| 2008/0009275 A1 | 1/2008 | Werner et al. | |
| 2008/0051993 A1 | 2/2008 | Graham et al. | |
| 2008/0058971 A1 | 3/2008 | Graham et al. | |
| 2008/0059064 A1 | 3/2008 | Werner et al. | |
| 2008/0065319 A1 | 3/2008 | Graham et al. | |
| 2008/0088303 A1 | 4/2008 | Englert | |
| 2008/0103689 A1 | 5/2008 | Graham et al. | |
| 2008/0125288 A1 | 5/2008 | Case | |
| 2008/0201100 A1 | 8/2008 | Petrov | |
| 2008/0274844 A1 | 11/2008 | Ward | |
| 2008/0319661 A1 | 12/2008 | Werner et al. | |
| 2009/0047645 A1* | 2/2009 | Dibenedetto | H04M 1/72563 434/258 |
| 2009/0048044 A1 | 2/2009 | Oleson et al. | |
| 2009/0048070 A1 | 2/2009 | Vincent et al. | |
| 2009/0233770 A1 | 9/2009 | Vincent et al. | |
| 2009/0292178 A1 | 11/2009 | Ellis et al. | |
| 2010/0009752 A1 | 1/2010 | Rubin et al. | |
| 2010/0042427 A1 | 2/2010 | Graham et al. | |
| 2010/0088023 A1 | 4/2010 | Werner | |
| 2010/0121599 A1 | 5/2010 | Boeve et al. | |
| 2010/0178994 A1* | 7/2010 | Do | A63D 15/006 473/2 |
| 2010/0184564 A1 | 7/2010 | Molyneux et al. | |
| 2010/0188397 A1 | 7/2010 | Tsai et al. | |
| 2010/0201352 A1 | 8/2010 | Englert | |
| 2010/0292050 A1 | 11/2010 | DiBenedetto et al. | |
| 2010/0292599 A1 | 11/2010 | Oleson et al. | |
| 2010/0292600 A1 | 11/2010 | Dibenedetto et al. | |
| 2011/0054270 A1 | 3/2011 | Derchak | |
| 2011/0054271 A1 | 3/2011 | Derchak et al. | |
| 2011/0054272 A1 | 3/2011 | Derchak | |
| 2011/0054290 A1 | 3/2011 | Derchak | |
| 2011/0082641 A1 | 4/2011 | Werner et al. | |
| 2011/0087115 A1 | 4/2011 | Sackner et al. | |
| 2011/0105861 A1 | 5/2011 | Derchak et al. | |
| 2011/0119022 A1 | 5/2011 | Kuenzler et al. | |
| 2011/0130643 A1 | 6/2011 | Derchak et al. | |
| 2012/0015779 A1 | 1/2012 | Powch et al. | |
| 2012/0083705 A1 | 4/2012 | Yuen et al. | |
| 2012/0254934 A1 | 10/2012 | McBrearty et al. | |
| 2012/0258433 A1 | 10/2012 | Hope et al. | |
| 2012/0290312 A1 | 11/2012 | Maruoka | |
| 2013/0009761 A1* | 1/2013 | Horseman | B60W 40/08 340/425.5 |
| 2013/0041590 A1 | 2/2013 | Burich et al. | |
| 2013/0095924 A1* | 4/2013 | Geisner | A63F 13/00 463/32 |
| 2013/0171596 A1* | 7/2013 | French | G09B 19/0038 434/236 |
| 2013/0208234 A1* | 8/2013 | Lewis | G06F 3/011 351/158 |
| 2013/0214998 A1 | 8/2013 | Andes et al. | |
| 2013/0274587 A1 | 10/2013 | Coza et al. | |
| 2013/0274635 A1 | 10/2013 | Coza et al. | |
| 2013/0274904 A1 | 10/2013 | Coza et al. | |
| 2013/0286004 A1 | 10/2013 | McCulloch et al. | |
| 2014/0266160 A1 | 9/2014 | Coza | |
| 2014/0309058 A1 | 10/2014 | San Juan | |
| 2014/0310595 A1* | 10/2014 | Acharya | G06F 9/4446 715/706 |
| 2014/0330411 A1* | 11/2014 | Lochmann | G01S 17/06 700/91 |
| 2014/0347265 A1* | 11/2014 | Aimone | G09G 3/003 345/156 |
| 2015/0328516 A1 | 11/2015 | Coza et al. | |

FOREIGN PATENT DOCUMENTS

| | | |
|---|---|---|
| EP | 1134555 A1 | 9/2001 |
| EP | 2 724 755 A1 | 4/2014 |
| JP | 07-96014 | 10/1995 |
| WO | WO 02/067449 A2 | 8/2002 |
| WO | WO 2012/014110 A2 | 2/2012 |

OTHER PUBLICATIONS

Extended European Search Report issued in European Application No. 15170976.3, mailed Jan. 7, 2016.

Yun, X., et al., "A Simplified Quaterrdon-Based Algorithm for Orientation Estimation From Earth Gravity and Magnetic Field Measurements," IEEE Transactions Instrumentation and Measurement, vol. 57, No. 3, pp. 638-650, Mar. 2008.

Shead, S., "Shirt Capable of Converting Body Heat into Electricity," The Engineer, https://www.theengineer.co.uk/issues/14-november-2011/shirt-capable-of-converting-body-heat-into-electricity/, article, dated Nov. 3, 2011, accessed Mar. 16, 2013.

Non-English language Office Action issued in Chinese Application No. 201310129427.7, mailed Dec. 29, 2014.

Non-English language Office Action issued in Chinese Application No. 201310128838.4, mailed Feb. 2, 2015.

Concise explanation of Office Action issued in Chinese Application No. 201310129427.7, mailed Dec. 29, 2014.

Concise explanation of Office Action issued in Chinese Application No. 201310128838.4, mailed Feb. 2, 2015.

Nonfinal Office Action issued in U.S. Appl. No. 15/593,954, mailed May 31, 2017.

* cited by examiner

ATHLETIC ACTIVITY HEADS UP DISPLAY SYSTEMS AND METHODS

FIELD OF THE INVENTION

Embodiments of the present invention generally relate to athletic activity heads up display systems and methods of using the same. More particularly, embodiments of the present invention relate to systems and methods for presenting computer-generated sensory input via a heads up display to an individual engaged in or observing an athletic activity, based on data related to the athletic activity.

BACKGROUND OF THE INVENTION

Athletic activity is important to maintaining a healthy lifestyle and is a source of entertainment for many people. Some individuals prefer to engage in team athletic activities such as, for example, soccer or basketball, while other individuals prefer to engage in individual athletic activities such as, for example, running or skiing. Regardless of whether the activity is a team or individual activity, it is common for individuals to participate in both competitive sessions, such as a soccer match or a running race, and more informal training sessions such as conducting soccer drills or running interval sprints. Others who do not themselves regularly take part in athletic activities may nevertheless enjoy viewing athletic activities as a spectator.

Athletic activity monitoring systems exist that are capable of recording information about an individual's performance during an athletic activity using sensors. Some portable fitness monitoring systems employ sensors attached to the individual's body, while other portable fitness monitoring systems rely on sensors attached to a piece of athletic equipment. Such sensors may be capable of measuring various physical and/or physiological parameters associated with the individual's athletic activity.

Technology has resulted in the development of so-called "heads up displays" (HUDs) for presenting visual information to a user without requiring the user to look away from their usual viewpoint. The origin of the term stems from airplane pilots being able to view information (e.g. flight status or plane orientation information) with their heads still positioned "up" and looking forward, instead of angled down looking at lower instruments. HUDs typically include a projector for projecting information onto a transparent surface, such as a glass plate, that enables the background environment of the user's typical viewpoint to still be seen. Although HUDs were initially developed for military aviation, they can now be found in commercial aircraft, automobiles, and computer gaming applications.

HUDs can be a useful tool for a variety of "augmented reality" applications. The basic idea of augmented reality is to present computer-generated sensory input to a user—superimposed graphics, audio, haptic feedback, or other sensory enhancements—that provide information about the environment and its objects in the context of a real-world environment. For example, fans of American football have become accustomed in recent years to the presence a superimposed "first-down" line on televised American football games.

An individual engaged in an athletic activity—or an interested observer such as a coach or fan—may desire to receive information about the athletic activity, including information about the individual's performance. But with respect to providing this information, existing athletic activity monitoring systems suffer from a number of drawbacks.

Many existing systems do not provide the individual or interested observer with information about the athletic activity until after the activity has been completed. Other systems may present the information about the athletic activity during the activity, but in a way that distracts that individual or interested observer from focusing on the ongoing athletic activity itself. And many existing HUDs and augmented reality systems are not portable and are therefore not suitable for monitoring in many real world athletic competitive or training sessions. Finally, existing athletic activity monitoring systems often fail to provide the individual or interested observer with quick, accurate, insightful information that would enable them to easily compare past performances, develop strategies for improving future performances, or visualize performances.

BRIEF SUMMARY OF THE INVENTION

What is needed are athletic activity heads up display systems and methods having improved capabilities over existing athletic activity monitoring systems, thus offering individuals engaged in athletic activities and other interested observers better tools to assess these activities. At least some of the embodiments of the present invention satisfy the above needs and provide further related advantages as will be made apparent by the description that follows.

Embodiments of the present invention relate to a method of using an athletic activity heads up display system during an athletic activity, including the steps of a heads up display unit receiving information about a sport ball, and the heads up display unit displaying an image to an individual based on the information, where the image is overlaid on the individual's present field of view of an environment.

Embodiments of the present invention also relate to a method of using an athletic activity heads up display system during an athletic activity, including the steps of a heads up display unit recognizing the presence of a sport ball in the heads up display unit's projected image field, and the heads up display unit displaying an image to an individual overlaid on the individual's present field of view of an environment, where the displayed image indicates an objective for the individual.

Embodiments of the present invention further relate to a method of using an athletic activity heads up display system during an athletic activity, including the steps of a heads up display unit determining a position of a part of the body of an individual wearing the heads up display during an athletic movement, and the heads up display unit displaying visual feedback to the individual about the position of the part of the body during the athletic movement.

Additional features of embodiments of the invention will be set forth in the description that follows, and in part will be apparent from the description, or may be learned by practice of the invention. Both the foregoing general description and the following detailed description are exemplary and explanatory and are intended to provide further explanation of the invention as claimed.

BRIEF DESCRIPTION OF THE FIGURES

The accompanying figures, which are incorporated herein, form part of the specification and illustrate embodiments of the present invention. Together with the description, the figures further serve to explain the principles of and to enable a person skilled in the relevant arts to make and use the invention.

DETAILED DESCRIPTION OF THE INVENTION

Figure 1:
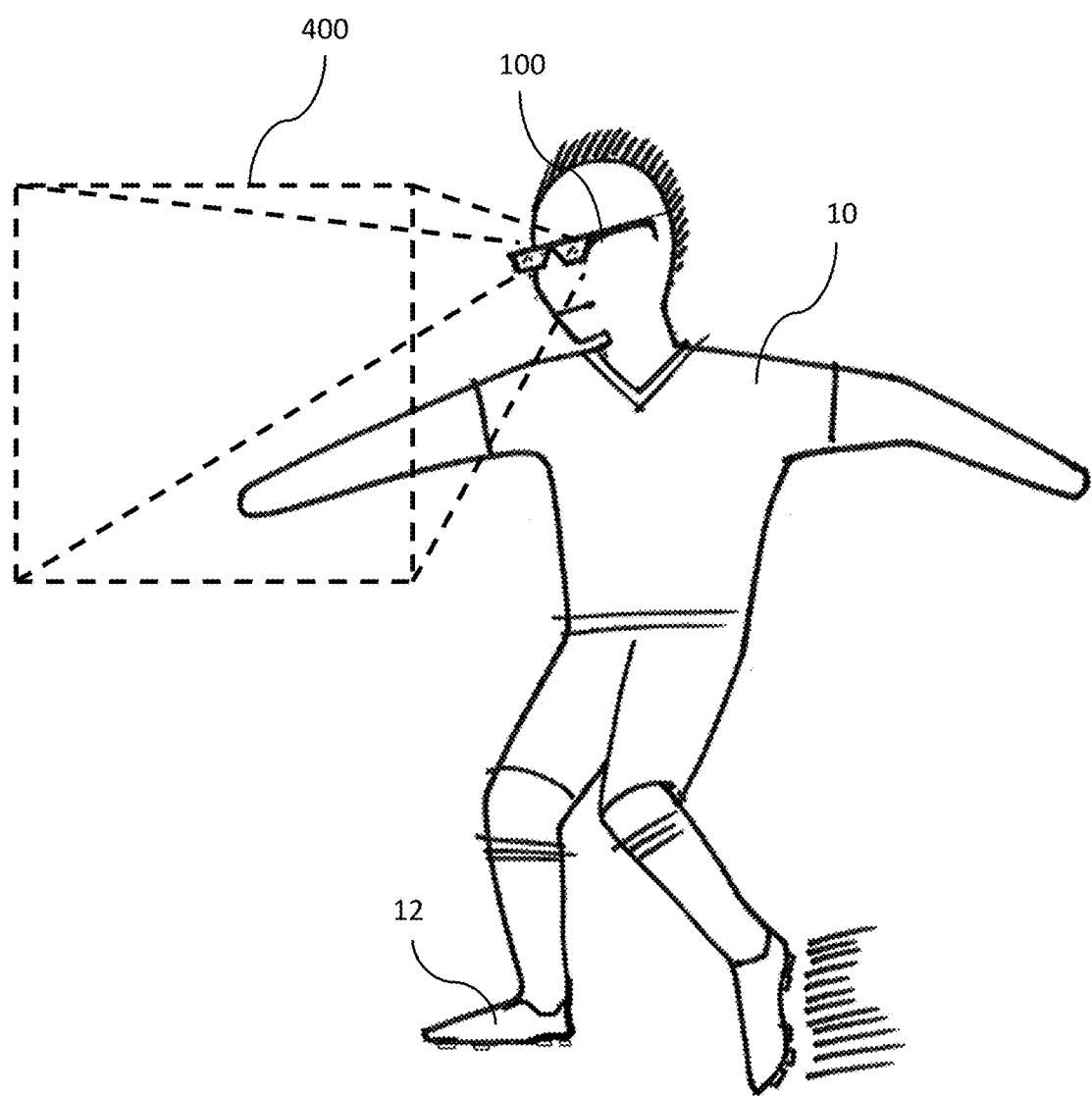
FIG. 1 is an illustration of an individual using a HUD according to an embodiment of the present invention.

The present invention will now be described in detail with reference to embodiments thereof as illustrated in the accompanying drawings. References to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The term "invention" or "present invention" as used herein is a non-limiting term and is not intended to refer to any single embodiment of the particular invention but encompasses all possible embodiments as described in the application.

Various aspects of the present invention, or any parts or functions thereof, may be implemented using hardware, software, firmware, non-transitory tangible computer readable or computer usable storage media having instructions stored thereon, or a combination thereof, and may be implemented in one or more computer systems or other processing systems.

The present invention generally relates to athletic activity "heads up display" (HUD) systems and methods of using the same during athletic activities. More particularly, embodiments of the present invention relate to systems and methods for presenting computer-generated sensory input via a HUD to an individual engaged in or observing an athletic activity, based on data related to the athletic activity.

An individual engaged in an athletic activity or an interested observer, such as a coach or fan, may desire to receive information about an athletic activity, including information about the individual's performance during the athletic activity. Existing athletic activity monitoring systems often disadvantageously present such information in a way that distracts that individual or interested observer from focusing on the ongoing athletic activity itself.

For example, when an individual engaged in an athletic activity must look away from the field of activity in order to view a visual output (e.g. a visual indicator of the individual's heart rate or the speed of a ball kicked by the individual), their level of attention, awareness, and concentration on the athletic activity is necessarily reduced. In the context of an ongoing competitive session (e.g. a soccer match), this risks a drop in the individual's performance and possibly risks injury to a distracted individual. Even in the context of a more informal non-competitive training session (e.g. conducting soccer drills), the distraction from having to look away from the individual's usual viewpoint can slowdown and therefore lengthen the training session and pull the individual out of their training "flow," possibly reducing the overall effectiveness of the training session.

Other interested individuals such as coaches or athletic activity spectators may be similarly disadvantaged by having to look away from the field of activity in order to view a visual output related to the athlete's performance.

In contrast, the athletic activity HUD systems and methods described herein aim to provide the individual or interested observer with quick, accurate, insightful information to enable them to easily and intuitively obtain information about the athlete's performance in a non-distracting manner, easily compare past performances, develop strategies for improving future performances, and/or visualize aspects of performances.

FIG. 1 is an illustration of an individual 10 using a HUD 100 according to an embodiment of the present invention. Generally speaking, HUDs 100 can be used to present visual information and/or other sensory input to a user without requiring the individual 10 to look away from their usual viewpoint.

The individual 10 depicted in FIG. 1 is engaged in the sport of soccer (i.e. football). While embodiments of the present invention will primarily be discussed with respect to the sport of soccer, the athletic activity HUD 100 systems and methods described herein may be suitable for use by individuals 10 or other interested individuals for team or individual athletic activities and for competitive and informal training sessions in other sports as well. For example, the athletic activity HUD 100 systems and methods described herein according to embodiments of the present invention may be suitable for use by individuals 10 engaged in athletic activities such as baseball, basketball, bowling, boxing, cricket, cycling, football (i.e., American football), golf, hockey, lacrosse, rowing, rugby, running, skateboarding, skiing, surfing, swimming, table tennis, tennis, or volleyball, or during training sessions related thereto.

The individual 10 depicted in FIG. 1 is equipped with a HUD 100 taking the form of a pair of glasses. While embodiments of the present invention will primarily be discussed with respect to HUDs 100 taking the form of a pair of glasses, the athletic activity HUD systems and methods described herein may also be incorporated into special purpose HUD hardware or other known objects of pieces of apparel such as hats, headbands, helmets, hoods, scarfs, shirts, pants, shoes, or safety gear.

Athletic activity HUDs 100 according to embodiments of the invention may superimpose graphics, audio, and other sensory enhancements over a real-world environment, possibly in real time. Athletic activity HUDs 100 may incorporate display technology that is capable of projecting one or more images in a way that makes them visible and overlaid on top of the individual's 10 "real world" view of their environment.

FIG. 1 illustrates an individual 10 playing soccer and wearing athletic activity HUDs 100 glasses. FIG. 1 further illustrates a representative projected image field 400 space within the individual's 10 field of view. The representative projected image field 400 represents a space within which the athletic activity HUDs 100 glasses are capable of projecting one or more images in a way that makes them visible and overlaid on top of the individual's 10 "real world" view of their environment.

The depicted projected image field 400 of FIG. 1 is representative in nature only. In some embodiments, the athletic activity HUD may include a projector for projecting information onto a transparent surface that is relatively close to the individual's eyes, such as the glass making up the lens of a pair of glasses or an adjacent glass plate. Nevertheless, from the perspective of the individual 10, the effective projected image field 400 could still be a relatively large area in the individual's 10 line of sight, such as the projected image field 400 depicted in FIG. 1.

In other embodiments of the present invention, the athletic activity HUD may include a projector for actually projecting information substantially further in front of the individual 10 onto other surfaces that effectively turn these surfaces into display surfaces. For example, the athletic activity HUD may project information onto the ground in front of the individual effectively turning the ground into a display surface.

Figure 2:
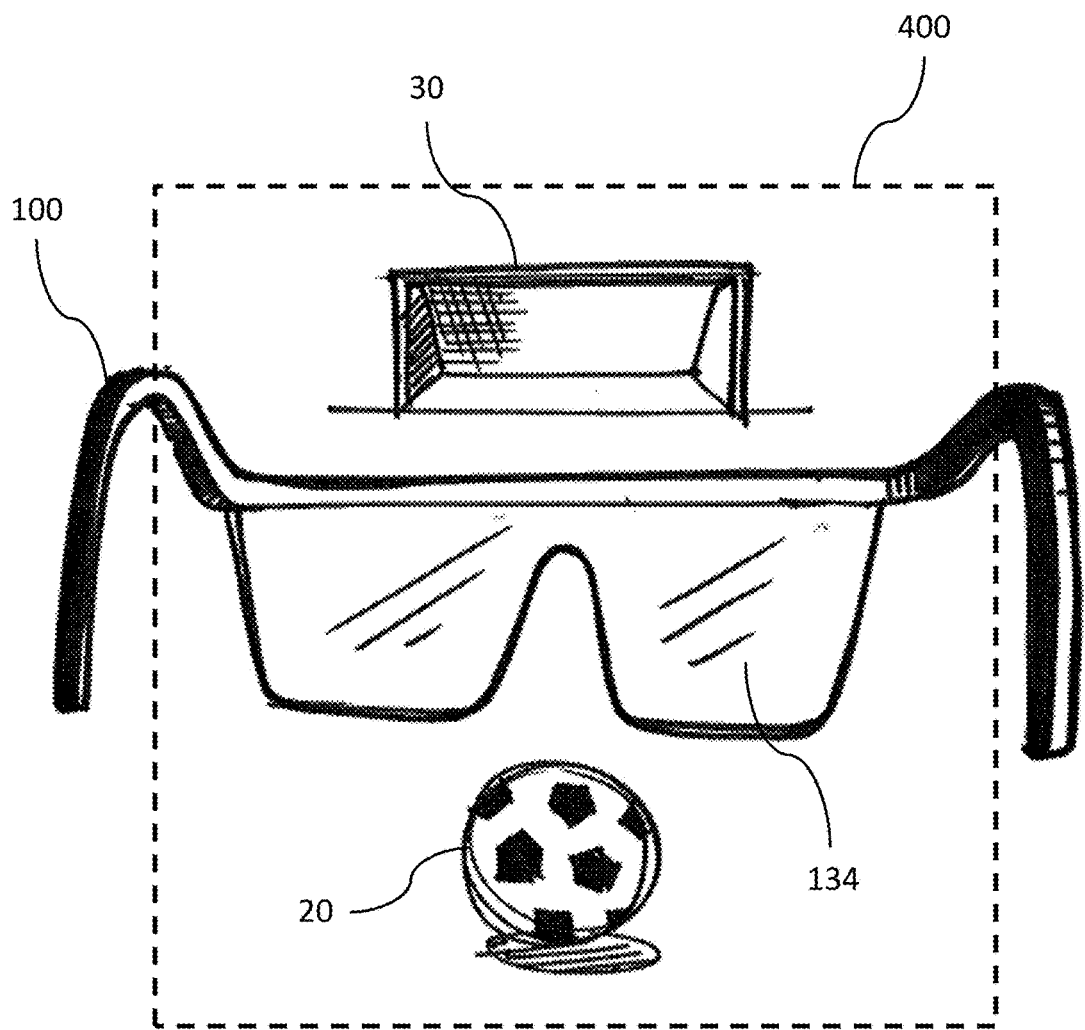
FIG. 2 is an illustration of an individual's view through a HUD including a projected image field according to an embodiment of the present invention.

FIG. 2 is an illustration of an individual's 10 view through a HUD 100 including a projected image field 400 according to an embodiment of the present invention. The projected image field 400 includes a real world view of a soccer ball 20 and a soccer goal 30, and does not include any overlaid images displayed by the HUD 100. This depiction is illustrative in nature only and may not represent an actual view seen by an individual. Specifically, while FIG. 2 illustrates both athletic activity HUD 100 glasses as seen from the back and the outlines of a projected image field 400, an individual wearing the athletic activity HUD 100 glasses and viewing the projected image field 400 may not actually visually perceive the frames of other components of the athletic activity HUD 100 glasses—other than any surfaces of the athletic activity HUD 100 glasses serving as a display surface for images projected for the individual 10 to view. Likewise, an individual not wearing the athletic activity HUD 100 glasses but viewing them from the back from some distance may not be able to perceive the projected image field 400.

Regardless of the nature of their projector configuration, Athletic activity HUDs 100 according to embodiments of the invention can be used to convey a wide variety of information to the individual 10 engaged in an athletic activity. For example, in some embodiments, an athletic activity HUD 100 may display general information to the individual such as the date, time, temperature, or location. This information may be conveyed, for example, as text visually overlaid in the projected image field 400.

The athletic activity HUD 100 may also display tips or guidance to the individual 10 such as tips or guidance on what to expect in their activity or sport, how they should attempt to perform a particular athletic maneuver, or what their objective should be for the activity or sport. In some embodiments, the tips or guidance may be conveyed, for example, as text visually overlaid in the projected image field 400.

Figure 3:
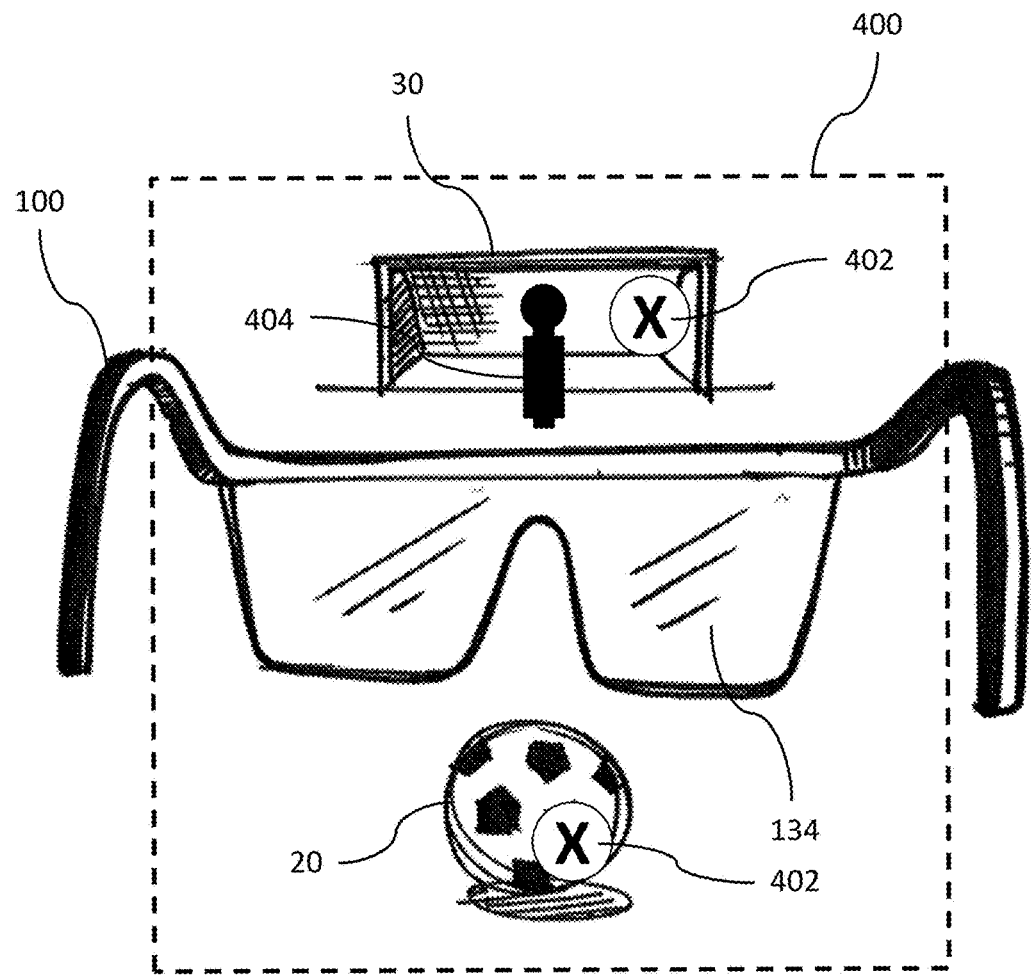
FIG. 3 is an illustration of an individual's view through a HUD including a projected image field according to an embodiment of the present invention.

In other embodiments, the tips or guidance may take the form of icons or other visual indicia such as a target icon 402 or an obstacle icon 404. FIG. 3 is another illustration of an individual's 10 view through a HUD 100 including a projected image field 400 according to an embodiment of the present invention. In this embodiment, the projected image field 400 includes a real world view of a soccer ball 20 and a soccer goal 30, and further includes a first target icon 402 overlaid on the real world soccer ball 20, a second target icon 402 overlaid on the real world soccer goal 30, and an obstacle icon 404 representing a goalie positioned in front of the real world soccer goal 30. The individual could be instructed to kick the soccer ball 20 so as to impact the soccer ball 20 with their foot 12 approximately at the location of the first target icon 402, to aim to direct the ball toward the second target icon 402, and around the obstacle icon 404 representing a goalie.

Figure 4:
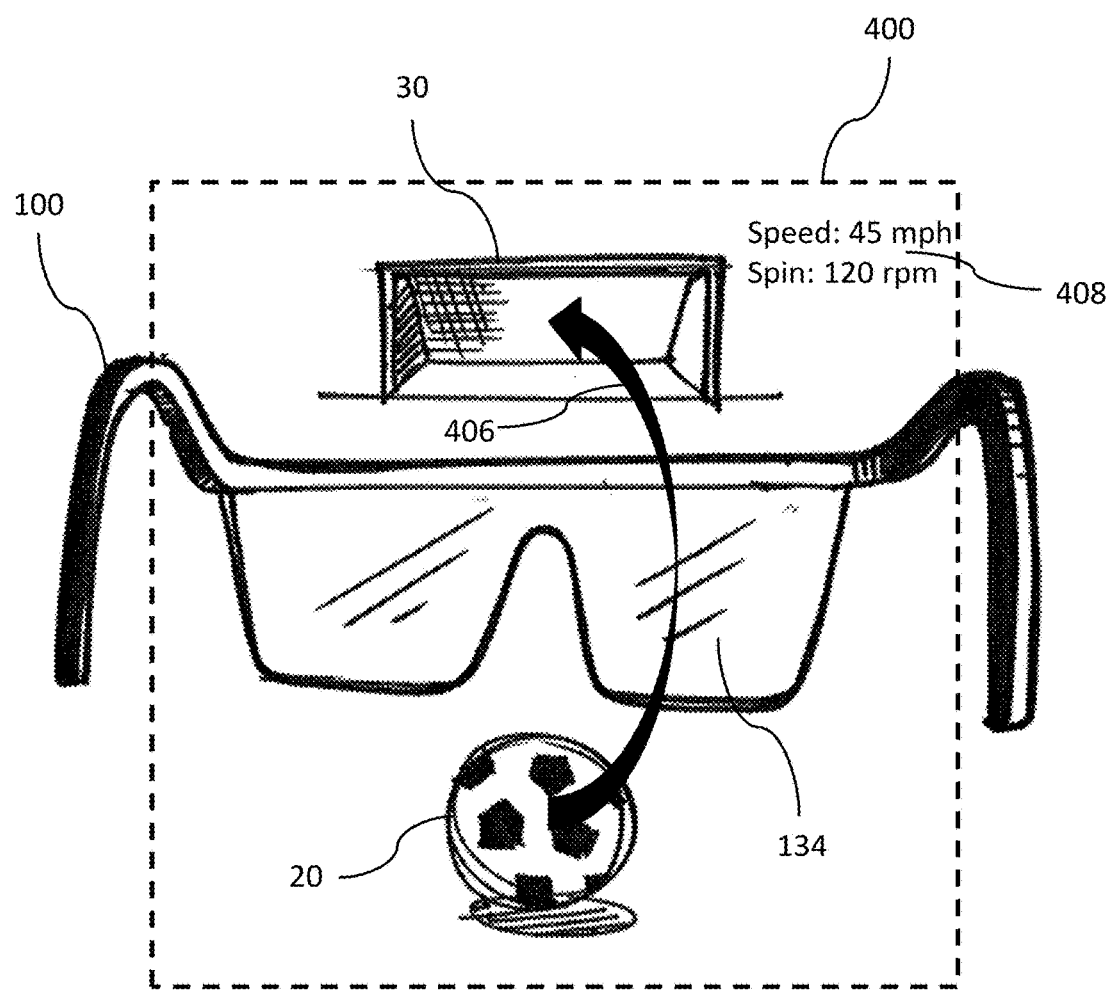
FIG. 4 is an illustration of an individual's view through a HUD including a projected image field according to an embodiment of the present invention.

In some embodiments, an athletic activity HUD 100 may be used to display athletic activity results or coaching based on data obtained during the athletic activity. FIG. 4 is an illustration of an individual's 10 view through a HUD 100 including a projected image field 400 according to an embodiment of the present invention. In this embodiment, the projected image field 400 again includes a real world view of a soccer ball 20 and a soccer goal 30, but this time further includes a flight path icon 406 and a feedback icon 408.

In the scenario where the individual 10 had just kicked a soccer ball 20 toward a soccer goal 30, the flight path icon 406 may be generated based on data obtained during the athletic activity, as explained in further detail below. In other words, the particular flight path depicted by the flight path icon 406 may be representative of an actual soccer ball 20 flight path from a soccer ball 20 kicked by the individual 10. Similarly, the feedback icon 408, which displays text indicating that the soccer ball's 20 speed was 45 miles per hour and that the soccer ball 20 was spinning at 120 revolutions per minute, may also be representative of the motion characteristics of an actual soccer ball 20 kicked by the individual 10.

In other embodiments, the athletic activity HUD 100 may be used to display images like those shown in FIG. 4 before a kick is to occur to indicate to the individual 10 that the depicted flight path and ball motion statistics are the objective for the individual 10 to achieve.

Figure 5:
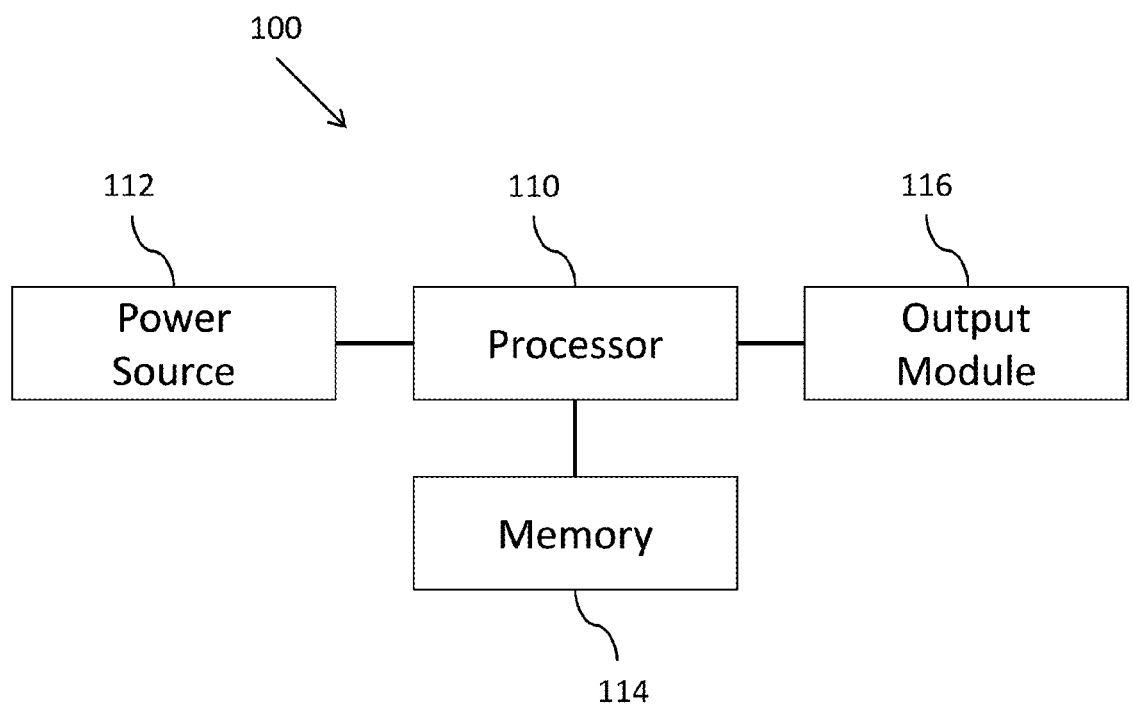
FIG. 5 is an illustration of the components of a HUD according to an embodiment of the present invention.

FIG. 5 is an illustration of exemplary components of a HUD 100 according to an embodiment of the present invention. In the illustrated embodiment, the HUD 100 includes a processor 110, a power source 112, a memory 114, and an output module 116 operatively connected to one another to carry out the functionality of the HUD 100. In other embodiments, one or more of these HUD 100 components may be omitted, or one or more additional components may be added.

The processor 110 may be adapted to implement application programs stored in the memory 114 of the HUD 100. The processor 110 may also be capable of implementing analog or digital signal processing algorithms such as raw data reduction and filtering. For example, processor 110 may be configured to receive raw data from sensors and process such data at the HUD 100. The processor 110 may be operatively connected to the power source 112, the memory 114, and the output module 116.

The power source 112 may be adapted to provide power to the HUD 100. In one embodiment, the power source 112 may be a battery. The power source may be built into the HUD 100 or removable from the HUD 100, and may be rechargeable or non-rechargeable. In one embodiment, the HUD 100 may be repowered by replacing one power source 112 with another power source 112. In another embodiment, the power source 112 may be recharged by a cable attached to a charging source, such as a universal serial bus ("USB") FireWire, Ethernet, Thunderbolt, or headphone cable, attached to a personal computer. In yet another embodiment, the power source 112 may be recharged by inductive charging, wherein an electromagnetic field is used to transfer energy from an inductive charger to the power source 112 when the two are brought in close proximity, but need not be plugged into one another via a cable. In some embodiment, a docking station may be used to facilitate charging.

The memory 114 of an exemplary HUD 100 may be adapted to store application program instructions and to store athletic activity data. In an embodiment, the memory 114 may store application programs used to implement aspects of the functionality of the athletic activity HUD 100 systems and methods described herein. In one embodiment, the memory 114 may store raw data, recorded data, and/or calculated data. In some embodiments, as explained in further detail below, the memory 114 may act as a data storage buffer. The memory 114 may include both read only memory and random access memory, and may further include memory cards or other removable storage devices.

In some embodiments of the present invention, the memory 114 may store raw data, recorded data, and/or calculated data permanently, while in other embodiments the memory 114 may only store all or some data temporarily, such as in a buffer. In one embodiment of the present invention, the memory 114, and/or a buffer related thereto, may store data in memory locations of predetermined size such that only a certain quantity of data may be saved for a particular application of the present invention.

The output module 116 of an exemplary HUD 100 may be a visual display output module 116 integrally coupled to the HUD 100. The visual display output module 116 may be used to visually display information to the individual 10. In an embodiment, the visual display output module 116 may include, for example, a liquid crystal display (LCD), a light-emitting diode (LED) display, or an organic light-emitting diode (OLED) display. In one embodiment, the output module 116 may be adapted to provide audio (e.g. via a speaker) and/or tactile (e.g. vibration) output in addition to or instead of visual display output.

Figure 6:
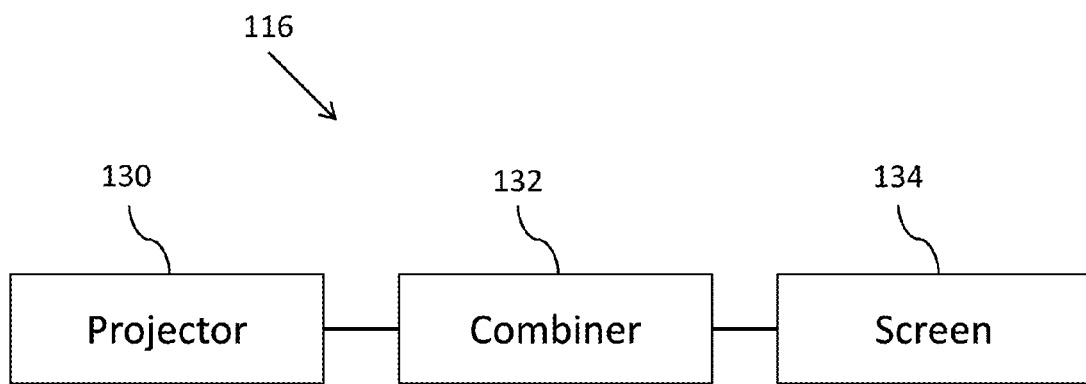
FIG. 6 is an illustration of the components of a HUD display module according to an embodiment of the present invention.

FIG. 6 is an illustration of the sub-components of a HUD 100 display output module 116 according to an embodiment of the present invention. In on embodiment, the HUD may include three primary components: a projector 130, a combiner 132, and a screen 134.

The projector 130 may be an optical collimator setup that includes a convex lens or concave mirror with a Cathode Ray Tube, light emitting diode, or liquid crystal display at its focus. This setup may produce an image where the light is "parallel" i.e. perceived to be at infinity. The processor 110 may provide the interface between the rest of the HUD 100 and the projector 130 such that the processor 110 generates the imagery to be displayed by the projector 130.

The combiner 132 may be an angled flat piece of glass (i.e. a beam splitter) located directly in front of the individual's eyes or field of vision that redirects the projected image from projector 130 in such a way as to be able to see the field of view (i.e. the background environment) and the projected infinity image at the same time. The combiner 132 may have a special coating that reflects light projected onto it from the projector 130 unit while allowing other light to pass through. In some embodiments, the combiner 132 may also have a curved surface to refocus the image from the projector 130.

The screen 134 may be a separate surface, such as a transparent or semi-transparent glass plate, that enables the background environment of the individual's 10 typical viewpoint to still be seen. In other words, the screen 134 may provide the basis for the individual to view the effective projected image field 400 in their field of view. In some embodiments, the combiner 132 and the screen 134 may be a single piece of hardware capable of serving the functions of both the combiner 132 and the screen 134.

Figure 7:
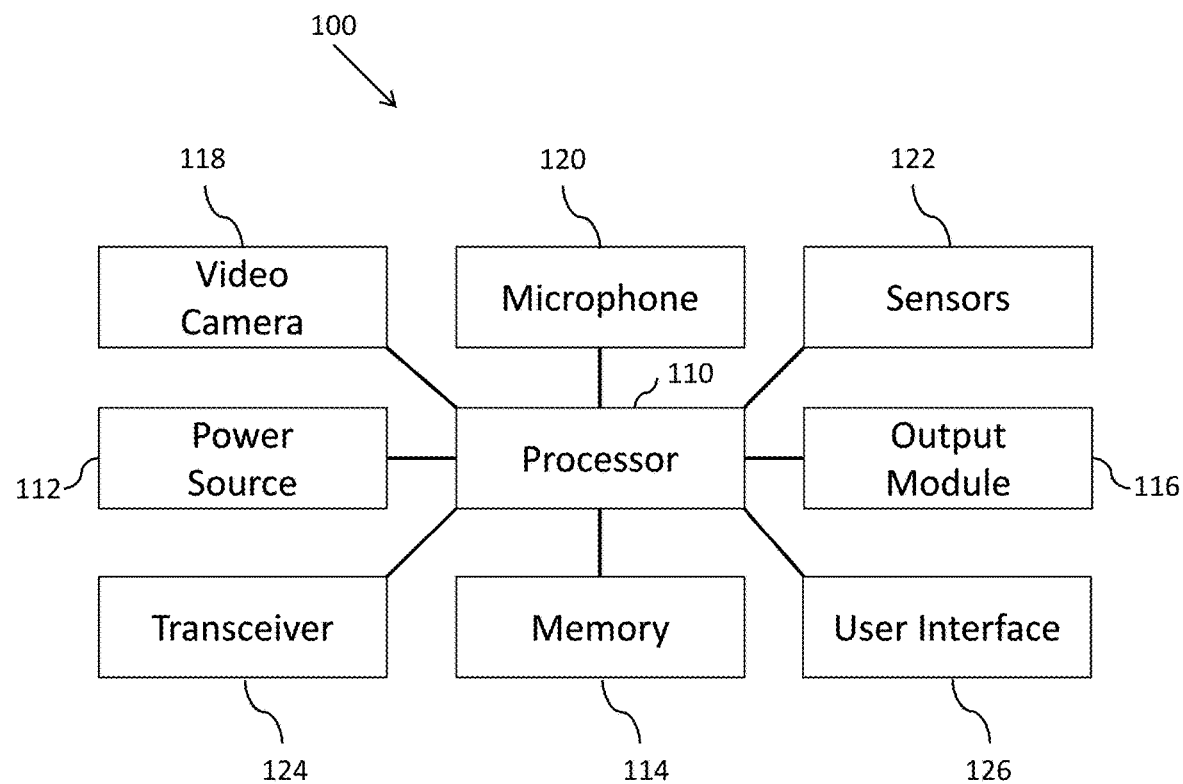
FIG. 7 is an illustration of the components of a HUD according to an embodiment of the present invention.

FIG. 7 is an illustration of the additional components of a HUD according to an embodiment of the present invention. The processor 110, power source 112, memory 114, and output module 116 illustrated in FIG. 7 may be similar to those illustrated in FIG. 5. In the embodiment illustrated in FIG. 7, the HUD 100 includes a processor 110, a power source 112, a memory 114, an output module 116, a video camera 118, a microphone 120, one or more sensors 122, a transceiver, and a user interface 126 operatively connected to one another to carry out the functionality of the HUD 100. In other embodiments, one or more of these HUD 100 components may be omitted, or one or more additional components may be added.

The video camera 118 may be any suitable video recording component, such as a digital video camera incorporated into the HUD 100. In some embodiments, the video camera 118 may be configured and oriented such that the video camera 118 may record a "first person" view of what the individual wearing the HUD 100 sees while engaged in their athletic activity. Any video recorded may be played back to the individual 10 or other interested individual in real time or after the recorded event. In some embodiments, the HUD may playback a recorded video that is annotated with other visual images, such as the images discussed throughout as being potentially displayed in the projected image field 400. In one embodiment, first person recorded video may be played back to the individual 10 wearing the HUD 100 such that the first person recorded video takes up the individual's 10 entire field of view. In this sense, the first person recorded video may provide a "virtual reality"-like experience to the individual 10. In another embodiment, the first person recorded video may be played back to the individual 10 wearing the HUD 100 such that the first person recorded video takes up less than the individual's 10 entire field of view. For example, the first person recorded video may be displayed in one corner of the individual's 10 field of view so that the individual 10 may view the video or shift their attention to other real world items in their field of view.

Incorporating a video camera 118 into an embodiment of an athletic activity HUD 100 may provide the athletic activity HUD 100 with additional capabilities. For example, athletic activity HUDs 100 according to embodiments of the invention incorporating a video camera 118 may be used to determine the orientation of the individual's 10 body to the ball 20, determine the orientation of the individual's 10 foot 12 to the ball 20, determine the orientation of the ball 20 to the goal 30 (i.e. determine when a goal is scored based on a recorded video image of the ball 20 entering the goal 30), determine the rotation rate or speed of the ball 20, determine the number of ball 20 touches, or even trigger the taking of a still photo or video clip by the HUD 100 based on a determination of foot 12-ball 30 impact.

In embodiments of the present invention where a video camera 118 is used to determine the relative orientation of the individual's 10 body or motion of a ball 20, certain optical motion tracking features may be employed. In some embodiments, video of the movements of one or more of a portion of the individual's 10 body or of a ball 20 are sampled many times per second. This resulting video data can be mapped in a three dimensional model so that the model can replicate the motion of the portion of the individual's 10 body or of the ball 20.

In other embodiments, the optical motion tracking features can be used to determine whether or not the recorded video image data contains some specific object, feature, or activity (e.g. a ball 20 or a ball being kicked into a goal 30). This can be accomplished, for example, by identifying a specific object (e.g. a ball 20) in specific situations that may be described in terms of well-defined illumination, background, and position of the object relative to the camera. For example, a ball 20 being kicked into a goal 30 could exhibit certain visual patterns of illumination, background, and position.

Some optical motion tracking features may rely on the correspondence of image features between consecutive frames of video, taking into consideration information such as position, color, shape, and texture. Edge detection can be performed by comparing the color and/or contrast of adjacent pixels, looking specifically for discontinuities or rapid changes.

In some embodiments, certain soccer techniques, drills, or types of contacts with a ball 20 may be distinguished from one another based on optical motion tracking data derived from a video camera 118. Dribbling involves the individual 10 running with the ball 20 near their feet under close control. Passing involves the individual 10 kicking (or otherwise permissibly contacting) the ball toward one of their teammates. Juggling is a drill that involves the individual 10 kicking (or otherwise permissibly contacting) the ball 20 repeatedly in the air without letting the ball 20 hit the ground between kicks. In one embodiment of the present invention, recorded video data from a video camera 118 may be used, for example, to identify whether a particular contact of a ball 20 involved, for example, a dribble, pass, or juggle based on the recorded video data. As explained in further detail below, while ball 20 impact data may be obtained using a smart sport ball 300, in some embodiments, the smart sport ball 300 may not be capable of determining the specific types of contacts with the smart sport ball 300 without additional data, such as video data.

The microphone 120 may be any suitable audio recording component. The microphone 120 may be used to receive voice commands from the individual 10 to control the HUD 100, to receive voice notes, to conduct telephone calls of other communications, or to capture other relevant sounds during the course of an athletic activity such as the sound of the athlete's 10 foot 12 contacting a soccer ball 20 during a kick, the sound of a coach calling out an instruction to the individual 10, or the sound of a referee's whistle blowing.

Incorporating a microphone 120 into an embodiment of an athletic activity HUD 100 may provide the athletic activity HUD 100 with additional capabilities. For example, athletic activity HUDs 100 according to embodiments of the invention incorporating a microphone 120 may be used to determine the number of ball 20 touches or to determine how "clean" a kick was based on the sound profile.

In some embodiments, the HUD 100 may incorporate one or more other additional sensors 122. For example, in some embodiments, the HUD may include one or more of an acceleration sensor, a heart rate sensor, a magnetic field sensor, a thermometer, an angular momentum sensor (e.g., a gyroscope), and a positioning system receiver. In other embodiments, one or more of these sensors 122 may be omitted, or one or more additional sensors may be added.

The acceleration sensor may be adapted to measure the acceleration of the HUD 100. Accordingly, when the HUD 100 is physically coupled to the individual 10, the acceleration sensor may be capable of measuring the acceleration of the individual's 10 body or portion of the individual's 10 body that the HUD 100 is coupled to, including the acceleration due to the Earth's gravitational field. In one embodiment, the acceleration sensor may include a tri-axial accelerometer that is capable of measuring acceleration in three orthogonal directions. In other embodiments one, two, three, or more separate accelerometers may be used.

A magnetic field sensor may be adapted to measure the strength and direction of magnetic fields in the vicinity of the HUD 100. Accordingly, when the HUD 100 is physically coupled to the individual 10, the magnetic field sensor may be capable of measuring the strength and direction of magnetic fields in the vicinity of the individual 10, including the Earth's magnetic field. In one embodiment, the magnetic field sensor may be a vector magnetometer. In other embodiments, the magnetic field sensor may be a tri-axial magnetometer that is capable of measuring the magnitude and direction of a resultant magnetic vector for the total local magnetic field in three dimensions. In other embodiments one, two, three, or more separate magnetometers may be used.

In one embodiment, the acceleration sensor and the magnetic field sensor may be contained within a single accelerometer-magnetometer module. In other embodiments, the HUD 100 may include only one of the acceleration sensor and the magnetic field sensor, and may omit the other if desired.

Exemplary magnetic field sensor systems having certain athletic performance monitoring features that may be advantageously used in concert with the athletic activity HUD 100 systems and methods of the present invention, are disclosed in commonly owned U.S. patent application Ser. No. 13/797,361, filed Mar. 12, 2013, the entirety of which is incorporated herein by reference thereto.

In addition to the acceleration sensor and the magnetic field sensor, other sensors that may be part of the HUD 100 or separate from but in communication with the HUD 100 may include sensors capable of measuring a variety of athletic performance parameters. The term "performance parameters" may include physical parameters and/or physiological parameters associated with the individual's 10 athletic activity. Physical parameters measured may include, but are not limited to, time, distance, speed, pace, pedal count, wheel rotation count, rotation generally, stride count, stride length, airtime, stride rate, altitude, strain, impact force, jump force, force generally, and jump height. Physiological parameters measured may include, but are not limited to, heart rate, respiration rate, blood oxygen level, blood lactate level, blood flow, hydration level, calories burned, or body temperature.

An angular momentum sensor, which may be, for example, a gyroscope, may be adapted to measure the angular momentum or orientation of the HUD 100. Accordingly, when the HUD 100 is physically coupled to the individual 10, the angular momentum sensor may be capable of measuring the angular momentum or orientation of the individual 10 or portion of the individual's 10 body that the HUD 100 is coupled to. In one embodiment, the angular momentum sensor may be a tri-axial gyroscope that is capable of measuring angular rotation about three orthogonal axis. In other embodiments one, two, three, or more separate gyroscopes may be used. In an embodiment, the angular momentum sensor may be used to calibrate measurements made by one or more of an acceleration sensor and a magnetic field sensor.

A heart rate sensor may be adapted to measure an individual's 10 heart rate. The heart rate sensor may be placed in contact with the individual's 10 skin, such as the skin of the individual's 10 chest, wrist, or head. The heart rate sensor may be capable of reading the electrical activity the individual's 10 heart.

A temperature sensor may be, for example, a thermometer, a thermistor, or a thermocouple that measures changes in the temperature. In some embodiments, the temperature sensor may primarily be used for calibration other sensors of the athletic activity HUD 100 system, such as, for example, the acceleration sensor and the magnetic field sensor.

In one embodiment, the athletic activity HUD 100 may include a positioning system receiver. The positioning system receiver may be an electronic satellite position receiver that is capable of determining its location (i.e., longitude, latitude, and altitude) using time signals transmitted along a line-of-sight by radio from satellite position system satellites. Known satellite position systems include the GPS system, the Galileo system, the BeiDou system, and the GLONASS system. In another embodiment, the positioning system receiver may be an antennae that is capable of communicating with local or remote base stations or radio transmission transceivers such that the location of the HUD 100 may be determined using radio signal triangulation or other similar principles.

In yet another embodiment, the positioning system may operate based upon magnetometer readings, such as the detection of local magnetic fields, as described in commonly owned U.S. patent application Ser. No. 13/797,361, filed Mar. 12, 2013. In one embodiment, an acceleration sensor can be used in conjunction with a magnetometer and gyroscope in order to calibrate motion and position determinations. For example, information indicative of change in motion, gravity, and change in direction can be obtained using the acceleration sensor. Angular movement can be obtained using the gyroscope, and the absolute "North" orientation or local magnetic field data, such as magnetic field intensity and/or direction, can be obtained using the magnetometer. These sensor readings can be used to determine, for example, the posture of an individual 10, gravity, position and orientation of individual 10 in space, and heading of individual 10.

In some embodiments, positioning system receiver data may allow the HUD 100 to detect information that may be used to measure and/or calculate position waypoints, time, location, distance traveled, speed, pace, or altitude.

Incorporating one or more of the above recited sensors into an embodiment of an athletic activity HUD 100 may provide the athletic activity HUD 100 with additional capabilities. For example, athletic activity HUDs 100 according to embodiments of the invention incorporating one or more of an acceleration sensor, a magnetic field sensor, an angular momentum sensor, and a positioning system receiver may be used to determine parameters such as the individual's step count, approach speed, body alignment, and form, as explained in further detail below. In other embodiments, the HUD 100 may determine which player out of a group of players kicked a ball 20 at a given time based on pattern matching based on a pattern generated from particular individual 10 sensor data profiles.

In other embodiments, the athletic activity HUD 100 may leverage the capabilities of a microphone 120 and an output module 116 taking the form of a speaker to allow for audio communication between multiple individuals 10 using athletic activity HUDs 100, or between an individual using an athletic activity HUD 100 and an individual using another communication device such as a telephone or a two way radio transceiver. In one embodiment, the athletic activity HUD 100 includes hardware suitable for communicating via a cellular communications network.

While the above description has focused on the various exemplary components and functionalities of an athletic activity HUD 100 in isolation, in other embodiments, one or more of the above recited components may instead or additionally be present in other devices that may be connected to the HUD 100 via a network to operate in concert with the HUD 100 to provide improved capabilities and functionalities for the individual 10 using the HUD 100.

Figure 8:
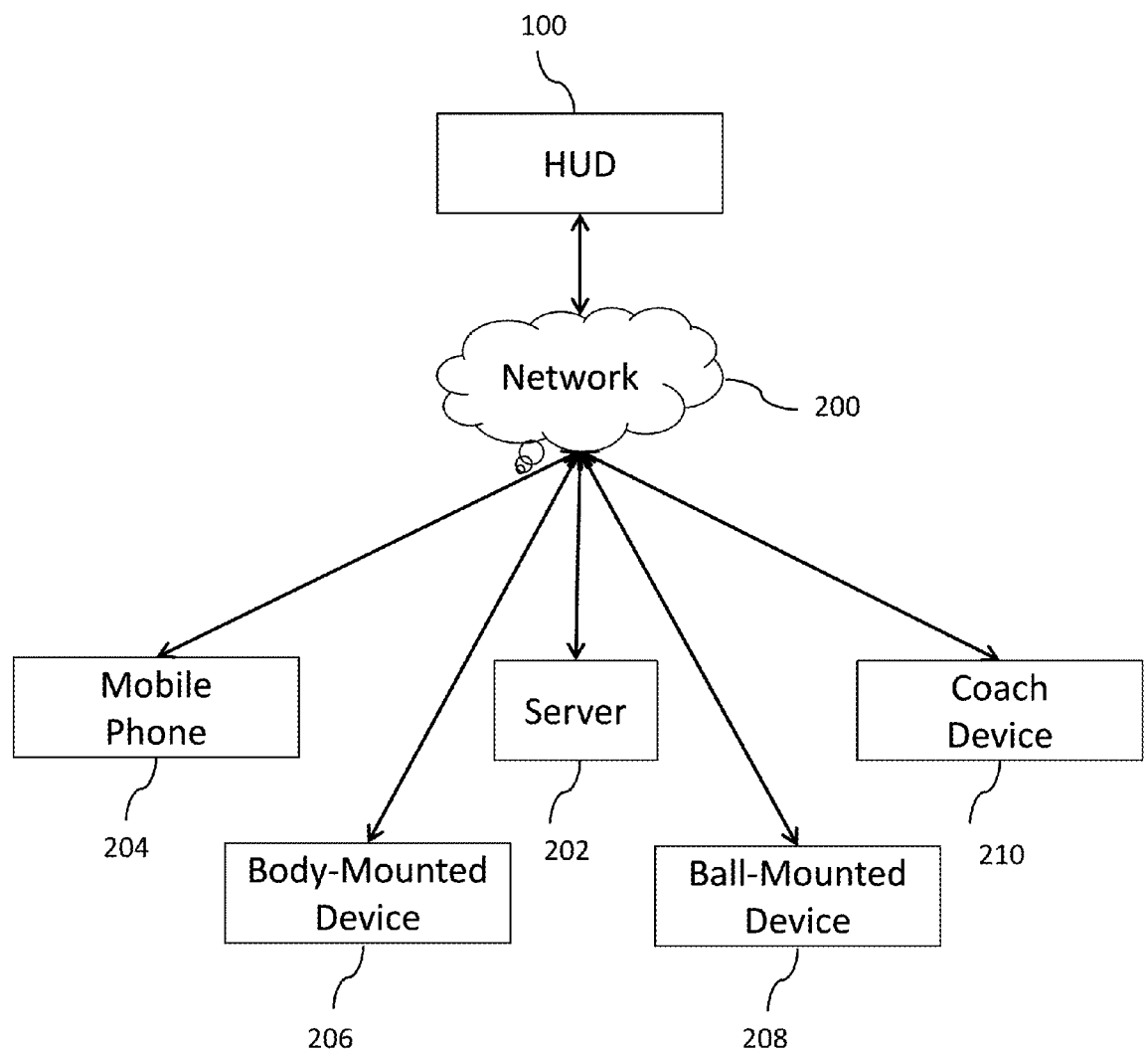
FIG. 8 is an illustration of a HUD communicating with a plurality of devices via a network according to an embodiment of the present invention.

Along these lines, FIG. 8 is an illustration of a HUD 100 communicating with a plurality of devices via a network 200 according to an embodiment of the present invention. In addition to HUD 100 and network 200, FIG. 8 illustrates a server 202, a mobile phone 204, a body-mounted device 206, a ball-mounted device 208, and a coach device 210.

In some embodiments of the present invention, the HUD 100 may communicate with one or more other components illustrated in FIG. 8 via wired or wireless technologies. Communication between the HUD 100 and other components may be desirable for a variety of reasons. For example, to the extent that the HUD 100 records and stores athletic activity information, it may be useful to transmit this information to another electronic device for additional data processing, data visualization, sharing with others, comparison to previously recorded athletic activity information, or a variety of other purposes. As a further example, to the extent that the HUD 100 has insufficient processing power, wide area network transmission capabilities, sensor capabilities, or other capabilities, these capabilities can be provided by other components of the system. With this in mind, possible communications means are described briefly below.

Wired communication between the HUD 100 and a personal computer (or other computing device) may be achieved, for example, by placing the HUD 100 in a docking unit that is attached to the personal computer using a communications wire plugged into a communications port of the personal computer. In another embodiment, wired communication between the sensor HUD 100 and the personal computer may be achieved, for example, by connecting a cable between the HUD 100 and the computer. The cable connecting the HUD 100 and the computer may be a USB cable with suitable USB plugs including, but not limited to, USB-A or USB-B regular, mini, or micro plugs, or other suitable cable such as, for example, a FireWire, Ethernet or Thunderbolt cable.

Wired connection to a personal computer or other computing device may be useful, for example, to upload athletic activity information from the HUD 100 to the personal computer or other computing device, or to download application software updates or settings from the personal computer or other computing device to the HUD 100.

Wireless communication between HUD 100 and the personal computer or other computing device may be achieved, for example, by way of a wireless wide area network (such as, for example, the Internet), a wireless local area network, or a wireless personal area network. As is well known to those skilled in the art, there are a number of known standard and proprietary protocols that are suitable for implementing wireless area networks (e.g., TCP/IP, IEEE 802.16, Bluetooth, Bluetooth low energy, ANT, ANT+ by Dynastream Innovations, or BlueRobin). Accordingly, embodiments of the present invention are not limited to using any particular protocol to communicate between the HUD 100 and the various elements depicted in FIG. 8.

In one embodiment, the HUD 100 may communicate with a wireless wide area network communications system such as that employed by mobile telephones. For example, a wireless wide area network communication system may include a plurality of geographically distributed communication towers and base station systems.

Communication towers may include one or more antennae supporting long-range two-way radio frequency communication wireless devices, such as HUD 100. The radio frequency communication between antennae and the HUD 100 may utilize radio frequency signals conforming to any known or future developed wireless protocol, for example, CDMA, GSM, EDGE, 3 G, 4 G, IEEE 802.x (e.g., IEEE 802.16 (WiMAX)), etc. The information transmitted over-the-air by the base station systems and the cellular communication towers to the HUD 100 may be further transmitted to or received from one or more additional circuit-switched or packet-switched communication networks, including, for example, the Internet.

As shown in FIG. 8, communication may also occur between the HUD 100, and one or more other computing devices such as a server 202, a mobile phone 204, a body-mounted device 206, a ball-mounted device 208, and/or a coach device 210 via a network 200. In an embodiment, the network 200 is the Internet. The Internet is a worldwide collection of servers, routers, switches and transmission lines that employ the Internet Protocol (TCP/IP) to communicate data. The network 200 may also be employed for communication between any two or more of the HUD 100, server 202, a mobile phone 204, a body-mounted device 206, a ball-mounted device 208, and/or a coach device 210.

A variety of information may be communicated between any of the network 200 may also be employed for communication between any two or more of the HUD 100, server 202, a mobile phone 204, a body-mounted device 206, a ball-mounted device 208, and/or a coach device 210, or other electronic components such as, for example, another HUD 100. Such information may include, for example, athletic performance information, device settings (including HUD 100 settings), software, and firmware.

Communication among these various elements may occur after the athletic activity has been completed or in real-time during the athletic activity.

Exemplary portable electronic device components, including mobile phones 204, having certain athletic performance monitoring features that may be advantageously used in concert with the athletic activity HUD 100 systems and methods of the present invention, are disclosed in commonly owned U.S. patent application Ser. No. 12/836,421, filed Jul. 14, 2010 (which published as U.S. Patent App. Pub. No. 2012/0015779), and commonly owned U.S. patent application Ser. No. 13/080,322, filed Apr. 5, 2011 (which published as U.S. Patent App. Pub. No. 2012/0258433) the entireties of which are incorporated herein by reference thereto.

Exemplary body-mounted devices 206 and/or ball-mounted devices 208, having certain athletic performance monitoring features that may be advantageously used in concert with the athletic activity HUD 100 systems and methods of the present invention, are disclosed in commonly owned U.S. patent application Ser. No. 13/446,937, filed Apr. 13, 2012 (which published as U.S. Patent App. Pub. No. 2013/0274635), commonly owned U.S. patent application Ser. No. 13/446,982, filed Apr. 13, 2012 (which published as U.S. Patent App. Pub. No. 2013/0274040), commonly owned U.S. patent application Ser. No. 13/797,274, filed Mar. 12, 2013 (which published as U.S. Patent App. Pub. No. 2013/0274587), and commonly owned U.S. patent application Ser. No. 14/120,272, filed May 14, 2014, the entireties of which are incorporated herein by reference thereto.

Exemplary coach devices 210 having certain athletic performance monitoring features that may be advantageously used in concert with the athletic activity HUD 100 systems and methods of the present invention are disclosed in commonly owned U.S. patent application Ser. No. 13/543,428, filed Jul. 6, 2012 (which published as U.S. Patent App. Pub. No. 2013-0041590), the entirety of which is incorporated herein by reference thereto.

More detailed examples of embodiments of the present invention that may utilize an athletic activity HUD 100—alone or in combination with one or more of a mobile phone 204, a body-mounted device 206, a ball-mounted device 208, and/or a coach device 210—the to provide athletic activity monitoring to individuals 10 engaged in athletic activities or other interested persons are provided below.

Figure 9:
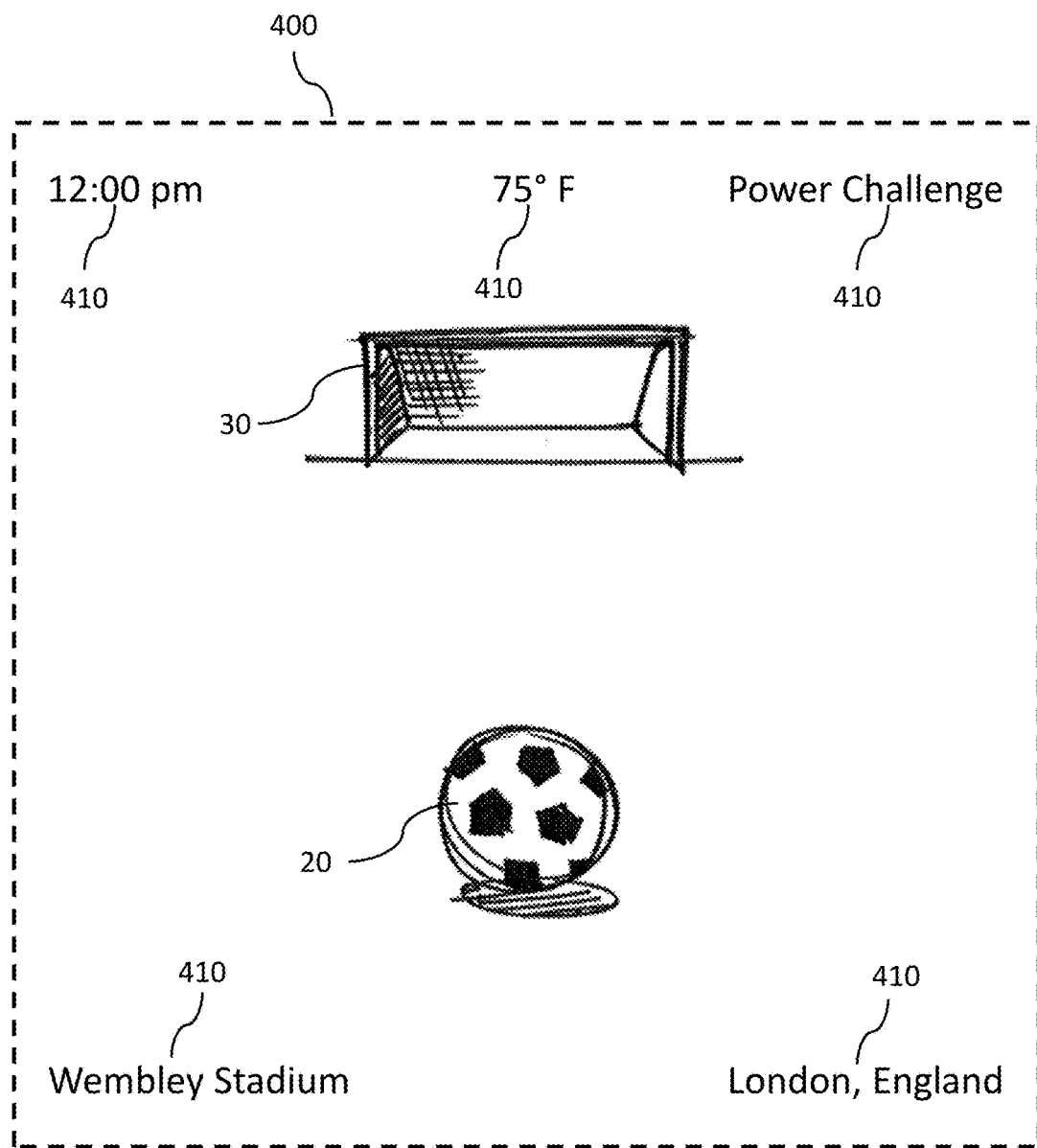
FIG. 9 is an illustration of a HUD projected image field according to an embodiment of the present invention.

FIG. 9 is an illustration of a HUD 100 projected image field 400 according to an embodiment of the present invention. Athletic activity HUDs 100 according to embodiments of the invention can be used to convey a wide variety of information to the individual 10 engaged in an athletic activity. For example, in the embodiment of FIG. 9, an athletic activity HUD 100 may display general information to the individual via information icons 410 such as the time of day (12:00 pm), the current temperature (75° F.), any particular operating mode that the HUD 100 is operating in (a "power challenge"), and the location of the HUD 100 (Wembley Stadium in London, England). As illustrated, this information may be conveyed, for example, as text visually overlaid in the projected image field 400. In other embodiments, additionally or alternatively, this information may be conveyed audibly to the individual 10 via an output module 116 including a speaker.

In some embodiments, in addition to being displayed to the individual 10 in an overlaid fashion in the projected image field 400 over the real world background of a soccer ball 20 and soccer goal 30 that the individual is looking at while wearing their HUD 100, the information displayed may also be recorded and/or transmitted to other devices such as a server 202, a mobile phone 204, a body-mounted device 206, a ball-mounted device 208, and/or a coach device 210 for storage, further processing, or display.

In embodiments where the individual is utilizing both a HUD 100 and a mobile phone 204 or similar device such as a smart watch, the information may be stored, processed, or displayed by the phone 204 or similar device.

Figure 10:
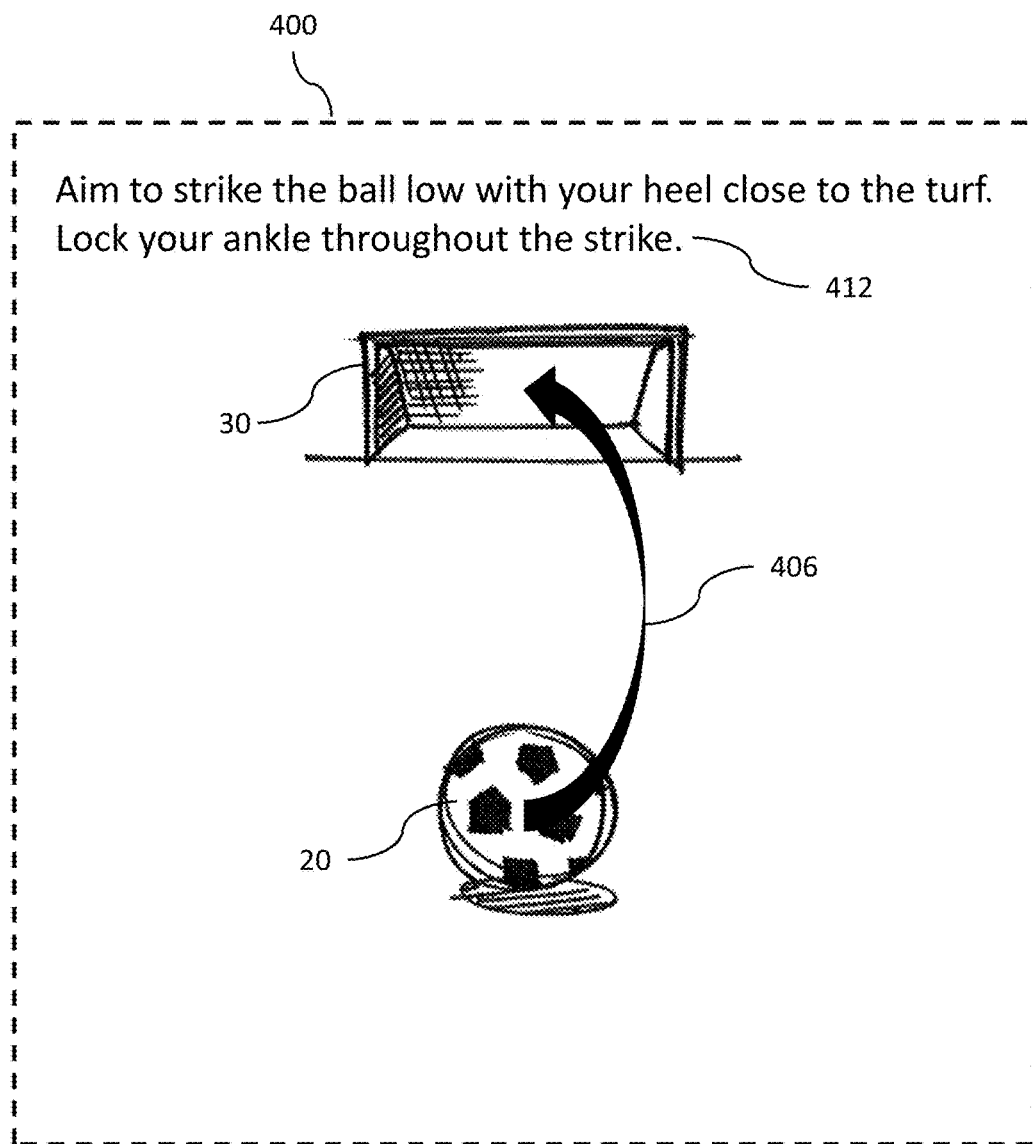
FIG. 10 is an illustration of a HUD projected image field according to an embodiment of the present invention.
Figure 11:
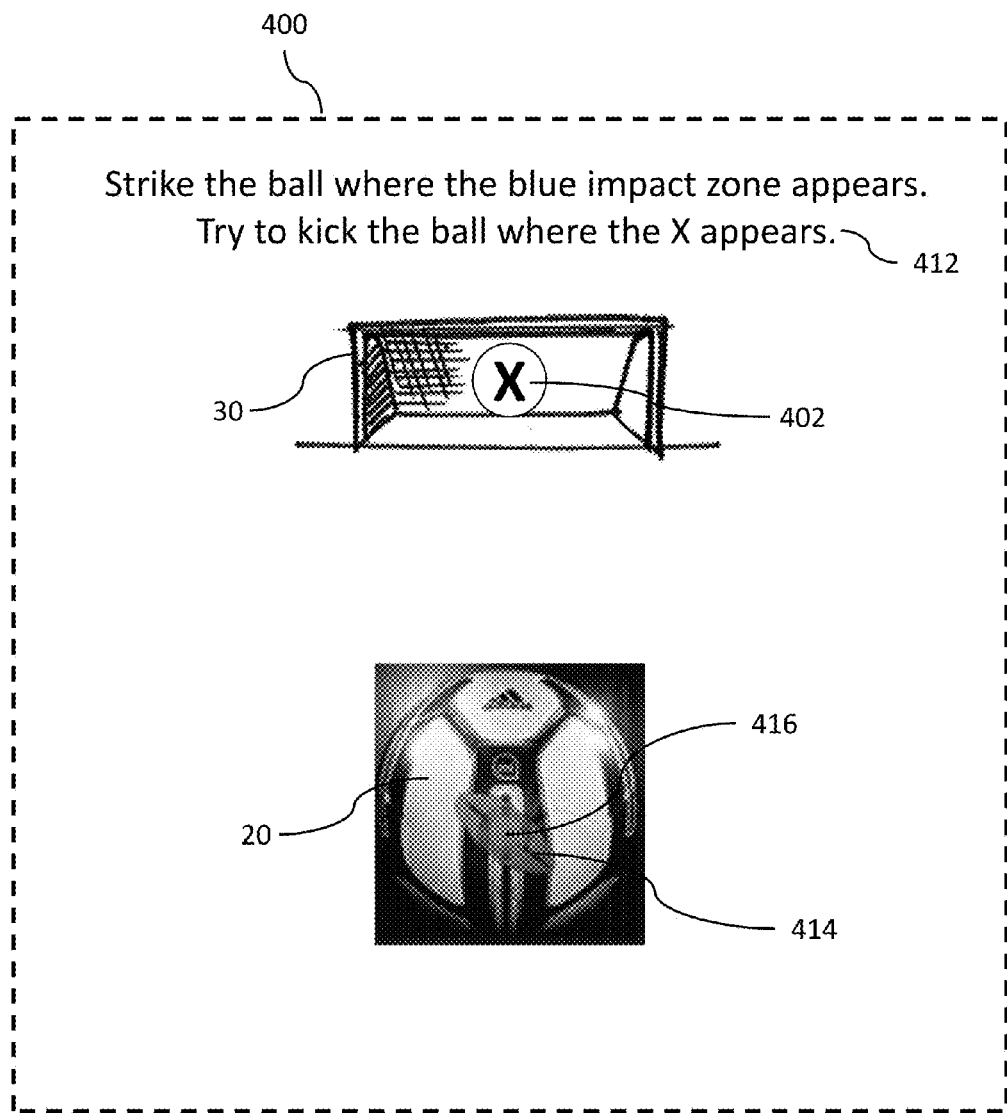
FIG. 11 is an illustration of a HUD projected image field according to an embodiment of the present invention.

FIG. 10 is an illustration of a HUD 100 projected image field 400 according to another embodiment of the present invention. In this embodiment, the athletic activity HUD 100 may display tips or guidance to the individual 10 within the projected image field 400. For example, the embodiment of FIG. 10 instructs the individual 10 to "aim to strike the ball low with your heel close to the turf. Lock your ankle throughout the strike." As depicted in FIG. 11, projected image field 400 may also include a flight path icon 406 displayed over the individual's 10 real world view of a soccer ball 20 and a soccer goal 30. The flight path icon 406 may display to the individual 10 the intended flight path of the kick.

In embodiments where the individual is utilizing both a HUD 100 and a mobile phone 204 or similar device such as a smart watch, this information may be stored, processed, or displayed by the phone 204 or similar device.

FIG. 10 is an illustration of a HUD 100 projected image field 400 according to yet another embodiment of the present invention. In this embodiment, tips or guidance to the individual 10 may take the form of icons or other visual indicia such as a target icon 402, a strike zone icon 414, and a point of impact icon 416. The illustrated projected image field 400 includes a real world view of a soccer ball 20 and a soccer goal 30, and further includes a target icon 402 overlaid on the real world soccer goal 30, and an overlapping strike zone icon 414 and a point of impact icon 416 overlaid on the real world soccer ball 20.

When an individual 10 kicks a soccer ball 20, the impact typically results in deformation of both the individual's 10 foot 12 (or rather, the footwear covering their foot 12) and of the soccer ball 20. Deformation of the soccer ball 20 is more significant and visually apparent—a surface of the soccer ball 20 typically becomes indented or flattened in response to a sufficiently swift kick. The "strike zone" represented by the strike zone icon 414 shown in FIG. 11 represents an area of the surface of the soccer ball 20 where contact with a portion of the individual's 10 foot 12 and/or deformation of the soccer ball 20 may occur during a kick. The "point of impact" represented by the point of impact icon 416 shown in FIG. 11 within the strike zone icon 414 occurs within the bounds of the strike zone, and represents the location on the surface of the soccer ball 20 that approximately coincides with the center of the area of the foot 12 in contact with the soccer ball 20.

In the embodiment of FIG. 11, the individual 10 could be instructed to kick the soccer ball 20 so as to impact the soccer ball 20 with their foot 12 approximately at the location corresponding to the strike zone icon 414 so that the center of the area of the individual's 10 foot 12 approximately at the location corresponding to the point of impact icon 416. Doing so may lead to a desired kick (e.g. a kick having a desired speed, spin, launch angle, etc.). And as explained in further detail below, embodiments employing a ball-mounted device 208 may be able to provide additional data for making such determinations.

In embodiments where the individual is utilizing both a HUD 100 and a mobile phone 204 or similar device such as a smart watch, this information may be stored, processed, or displayed by the phone 204 or similar device.

In addition, in embodiments where the individual is utilizing a HUD 100 that incorporates one or more of the above recited sensors, such as an acceleration sensor, a magnetic field sensor, an angular momentum sensor, or a positioning system receiver, the HUD 100 may be used to determine parameters such as the individual's step count, approach speed, body alignment, and form.

Figure 12:
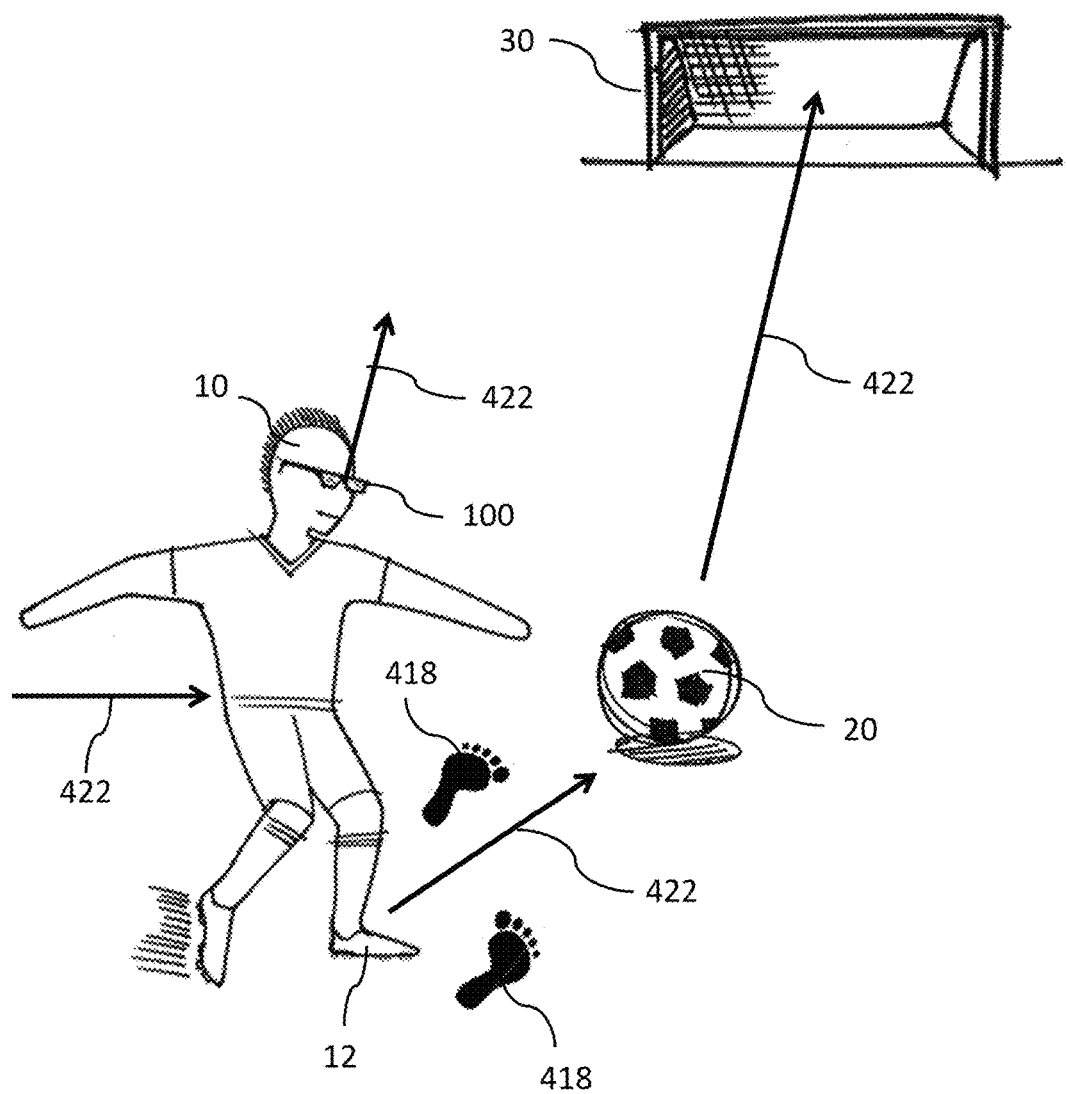
FIG. 12 is an illustration of an individual using a HUD according to an embodiment of the present invention.

FIG. 12 is an illustration of an individual 10 using a HUD 100 according to an embodiment of the present invention. In this embodiment, footstep icons 418 are representative of the locations that the individual 10 may step before kicking a ball 20. In one embodiment, step count may be determined by sensing vibrations at the HUD 100. In embodiments where the individual 10 is also carrying a mobile phone 204, step count may be determined by sensing vibrations at the HUD 100, the mobile phone 204 carried by the individual 10, or both.

Similarly, the individual's 10 approach speed, such as when running towards a ball 20 to kick the ball 20, may be determined by sensing motion of the HUD 100. In embodiments where the individual 10 is also carrying a mobile phone 204, speed may be determined by the HUD 100, the mobile phone 204 carried by the individual 10, or both.

In one embodiment, a HUD 100 projected image field 400 may include footstep icons 418 or other visual indicia that indicate to the individual 10 where they should step and with which foot (left or right) to perform specific soccer movements or drills. For example, a projected image field 400 could includes a real world view of a soccer ball 20 and a soccer goal 30 laid out across a soccer field, and further include footstep icons 418 overlaid on the real world soccer field. In an embodiment, the HUD 100 projected image field 400 may include three footstep icons 418 leading toward the real world view of a soccer ball 20 indicating to the individual 10 that they should step with their left foot, their right foot, and there left foot once more before striking the ball 20 with their right foot in order to execute a desired maneuver (e.g. kick the ball 20 toward the goal 30, pass the ball, etc.). In some embodiments, another footstep icon 418 may appear on or near the ball 20 indicating that the individual 10 should kick the ball 20 there, while in other embodiments a different icon or other visual indicia may appear on or near the ball 20 indicating that the individual 10 should kick the ball 20 there.

In another embodiment of the present invention, footstep icons 418 may be presented in a manner that conveys to the individual 10 a desired speed, timing, or cadence with which they should approach the ball. For example, the footstep icons 418 may be displayed one after another in series at specific times, such as one footstep every half second, or the second footstep a half a second after the first and the third footstep a quarter of a second after the third. In this way, the footstep icons 418 may be displayed so as to provide an animation of where and when the individual's steps approaching the ball 20 for a soccer maneuver should occur.

In some embodiments, the individual may be give specific drills to improve their skills. For example, the individual might be given coaching to bounce a ball 20 off a wall with the same cadence as that presented in the projected image field 400, via a speaker, or based on a transmitted vibration of the HUD 100. As explained in detail previously, in one embodiment of the present invention, recorded video data from a video camera 118 may be used, for example, to identify whether a particular contact of a ball 20 involved, for example, a dribble, pass, or juggle based on the recorded video data. Likewise, recorded video data can be used to determine if an individual 10 conducting drills has made good contact with the ball 20, or if the ball merely dropped or hit the ground.

Another popular and effective soccer drill is known as "wall ball." In one embodiment, this soccer skill building game can be enhanced using the HUD 100 according to embodiments of the present invention. For example, the individual 10 wearing the HUD 100 may be given a target on the wall in the projected image field 400 to strike with their real world ball 20. The software of the HUD 100 may be adapted to constantly vary the target area to force the individual 10 to react to the ball 20 as it strikes the wall at different angles. Such a system could build in a timing or cadence aspect to the game to help improve reaction time and moderating strike force.

In another embodiment, the HUD 100 could provide via its projected image field 400 the effect of a "virtual target" beyond a real world wall in front of the individual 10. For example, an individual 10 stationed in front of a wall may be able to kick a ball 20 off a wall while having the HUD 100 display in its projected image field 400 the virtual flight path the ball 20 would have taken had the individual 10 not been kicking directly into a wall. In this sense, the individual could achieve an experience somewhat similar to what is experienced by golfers hitting golf balls into projection screens on virtual courses, but without the constraints included in such systems. In this way, individuals 10 could practice making long outlet passes with moving targets (i.e. visually displayed via projected image field 400) without the hassle of being forced to retrieve the ball 20 from a great distance.

Providing the individual 10 with guidance on a desired footstep location and/or timing may enable the individual 10 better perform specific kicks or other maneuvers, become accustomed to a proper "pace" of conducting specific maneuvers, or improve the individual's 10 form for such maneuvers.

In one embodiment of the present invention, the individual's 10 HUD 100 projected image field 400 may include other types of guidance as to where and how they should move. For example, the individual 10 could be presented with a first person representation of desired motions (e.g. leg, foot, arm, and/or hand motions) that they should try to match to achieve a certain objective. In an embodiment, the individual 10 could be presented with a first person representation of how their feet may have to move to dribble a ball 20 with their feet in a certain manner. In some embodiments the individual's 10 HUD 100 projected image field 400 may include virtual obstacles such as defenders that the individual would have to dribble around. The individual 10 could be visually coached to dribble around or juke past the virtual defender. In other embodiments, the coaching provided by in the projected image field 400 may instead illustrate how the individual's 10 feet may have to move to dribble a ball 20 with their feet in a certain manner by illustrating an exemplary player conduction the motions (e.g. not a first person representation).

Finally, an individual's body alignment or form may be determined by sensing the orientation of one or more body parts of the individual based on acceleration sensor, magnetic field sensor, and/or angular momentum sensor data from the HUD 100. As illustrated in FIG. 12, orientation vectors 422 representing relative orientations of the individual's HUD 100, the individuals' 10 body orientation when moving toward the ball, the individual's 10 foot orientation in kicking the ball 20, and the orientation of the ball moving toward the goal 30. One or more of these vectors may be determined using suitable sensor data from the HUD 100. And in embodiments where the individual 10 is also carrying a mobile phone 204, one or more of these vectors may be determined using suitable sensor data from the HUD 100, the mobile phone 204 carried by the individual 10, or both. For example, a HUD mounted to the individual's 10 head and a mobile phone 204 carried in the individual's 10 pocket or attached to their arm may provide discrete data sets for determining different orientation vectors, how they relate to one another, and how this signifies the individual's 10 body alignment. This information can be used to provide feedback or other coaching to the individual on how their alignment impacts their athletic performance, including the motion metrics of their kicks.

Figure 13:
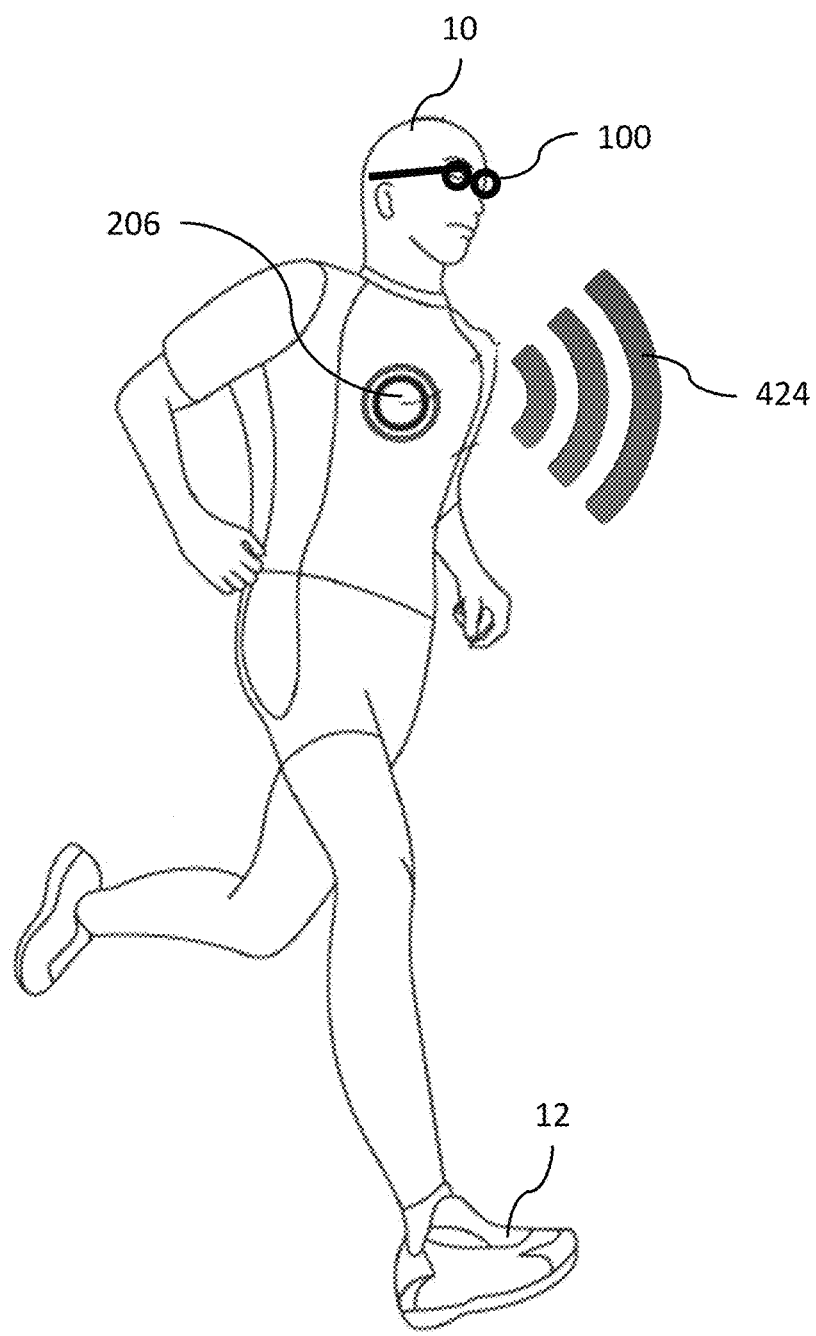
FIG. 13 is an illustration of an individual using a HUD and a body-mounted device according to an embodiment of the present invention.

FIG. 13 is an illustration of an individual 10 using a HUD 100 and a body-mounted device 206 according to an embodiment of the present invention. Suitable body-mounted devices 206 for use with the present invention are disclosed in commonly owned U.S. patent application Ser. No. 13/797,274, filed Mar. 12, 2013 (which published as U.S. Patent App. Pub. No. 2013/0274587). An individual 10 is wearing a HUD 100 taking the form of a pair of eyeglasses and also wearing a body-mounted device 206 secured to the individual's 10 chest. As illustrated and described above, the HUD 100 and the body-mounted device 206 may be capable of wireless communication with one another, such as personal area network communication via protocols such as Bluetooth, Bluetooth low energy, ANT, ANT+, or BlueRobin.

The features of embodiments of a HUD 100 system described above where the HUD 100 incorporates one or more of the above recited sensors, such as an acceleration sensor, a magnetic field sensor, an angular momentum sensor, or a positioning system receiver, may additionally or alternatively be provided in including a HUD 100 as well as a body-mounted device 206 including one or more of the above recited sensors, such as an acceleration sensor, a magnetic field sensor, an angular momentum sensor, or a positioning system receiver. In such a system, the body-mounted device 206 may be used to determine parameters such as the individual's step count, approach speed, body alignment, and form.

Specifically, in embodiments where the individual 10 is also wearing a body-mounted device 206, such as a chest body-mounted device 206, step count may be determined by sensing vibrations at the HUD 100, the body-mounted device 206 carried by the individual 10, or both.

Similarly, the individual's 10 approach speed, such as when running towards a ball 20 to kick the ball 20, may be determined by sensing motion of the HUD 100, the body-mounted device 206 carried by the individual 10, or both.

Finally, an individual's body alignment or form may be determined by sensing the orientation of one or more body parts of the individual based on acceleration sensor, magnetic field sensor, and/or angular momentum sensor data from the HUD 100. And in embodiments where the individual 10 is also wearing a body-mounted device 206, such as a chest body-mounted device 206, one or more of these vectors illustrated in FIG. 12 may be determined using suitable sensor data from the HUD 100, the chest body-mounted device 206, or both.

For example, a HUD mounted to the individual's 10 head and a chest body-mounted device 206 may provide discrete data sets for determining different orientation vectors, how they relate to one another, and how this signifies the individual's 10 body alignment. This information can be used to provide feedback or other coaching to the individual on how their alignment impacts their athletic performance, including the motion metrics of their kicks.

Figure 14:
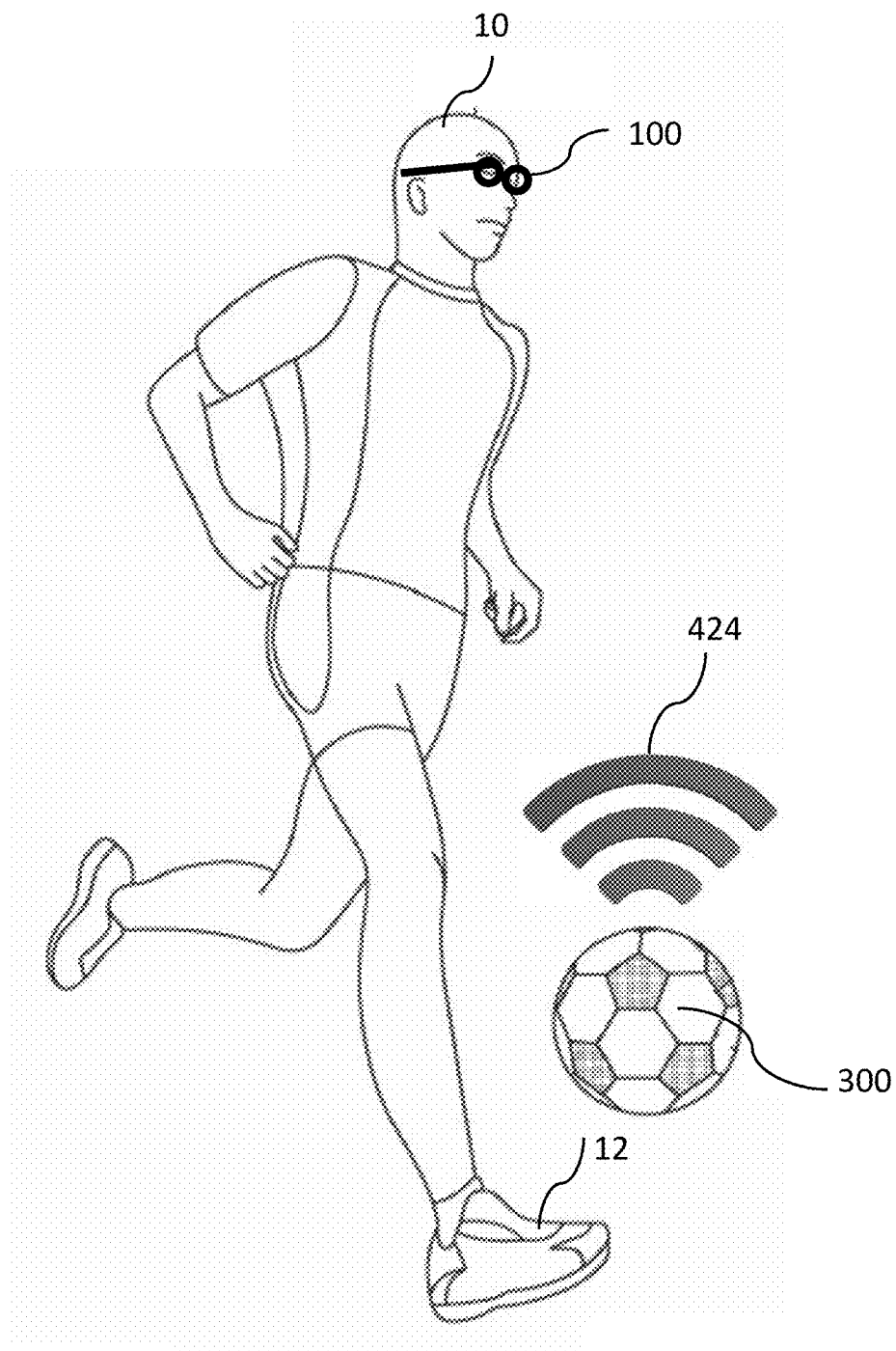
FIG. 14 is an illustration of an individual using a HUD and a sport ball-mounted device according to an embodiment of the present invention.

FIG. 14 is an illustration of an individual 10 using a HUD 100 and a sport ball-mounted device 208 according to an embodiment of the present invention. Suitable sport ball-mounted devices 208 for use with the present invention are disclosed in commonly owned U.S. patent application Ser. No. 13/446,982, filed Apr. 13, 2012 (which published as U.S. Patent App. Pub. No. 2013/0274040) and commonly owned U.S. patent application Ser. No. 14/120,272, filed May 14, 2014. An individual 10 is wearing a HUD 100 taking the form of a pair of eyeglasses and also using a sport ball-mounted device 208 taking the form of a "smart" soccer ball 300. As illustrated and described above, the HUD 100 and the sport ball-mounted device 208 may be capable of wireless communication with one another, such as personal area network communication via protocols such as Bluetooth, Bluetooth low energy, ANT, ANT+, or BlueRobin.

Figure 15:
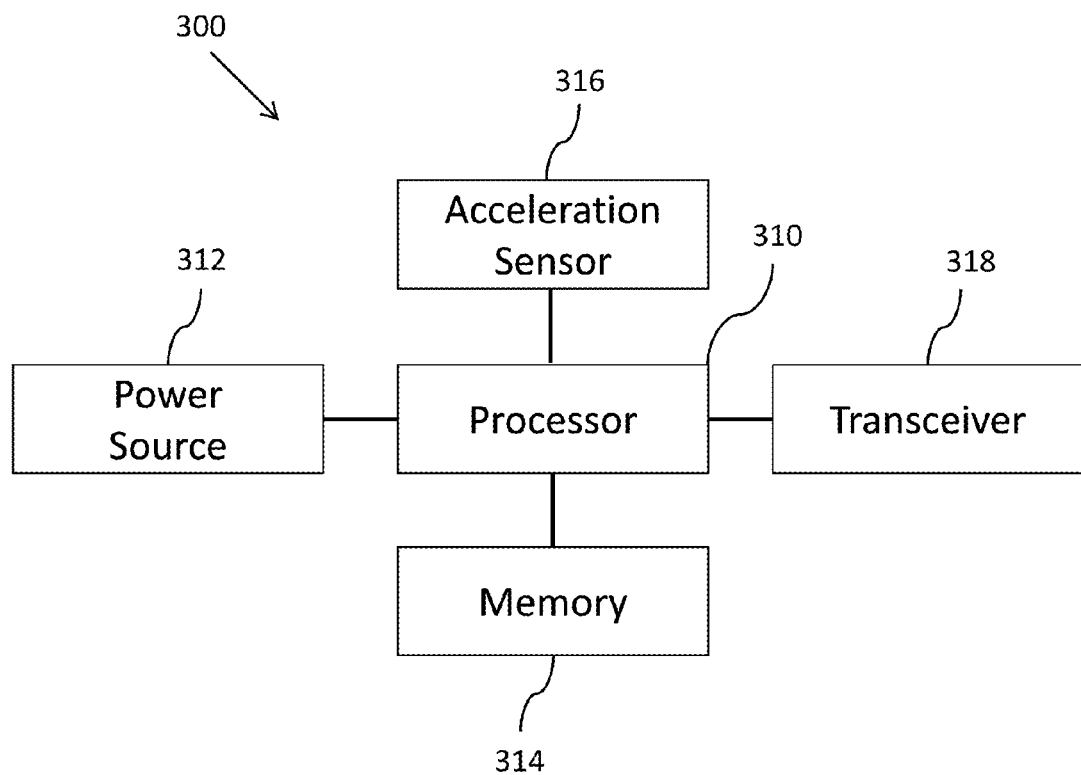
FIG. 15 is an illustration of the components of a sport ball according to an embodiment of the present invention.

FIG. 15 is an illustration of the components of a smart sport ball 300 according to an embodiment of the present invention. In the illustrated embodiment, the ball-mounted device 208 of the smart sport ball 300 includes a processor 310, a power source 312, a memory 314, an acceleration sensor 316, and a transceiver 318 operatively connected to one another to carry out the functionality of the smart sport ball 300. In other embodiments, one or more of these smart sport ball 300 components may be omitted, or one or more additional components may be added.

The processor 310 may be adapted to implement application programs stored in the memory 314 of the smart sport ball 300. The processor 310 may also be capable of implementing analog or digital signal processing algorithms such as raw data reduction and filtering. For example, processor 310 may be configured to receive raw data from sensors and process such data at the smart sport ball 300. The processor 310 may be operatively connected to the power source 312, the memory 314, the transceiver 318, and the acceleration sensor 316.

The power source 312 may be adapted to provide power to the smart sport ball 300. In one embodiment, the power source 312 may be a battery. The power source may be built into the smart sport ball 300 or removable from the smart sport ball 300, and may be rechargeable or non-rechargeable. In one embodiment, the smart sport ball 300 may be repowered by replacing one power source 312 with another power source 312. In another embodiment, the power source 312 may be recharged by a cable attached to a charging source, such as a universal serial bus ("USB") FireWire, Ethernet, Thunderbolt, or headphone cable, attached to a personal computer. In yet another embodiment, the power source 312 may be recharged by inductive charging, wherein an electromagnetic field is used to transfer energy from an inductive charger to the power source 312 when the two are brought in close proximity, but need not be plugged into one another via a cable. In some embodiment, a docking station may be used to facilitate charging.

The memory 314 of an exemplary smart sport ball 300 may be adapted to store application program instructions and to store athletic activity data, such as motion data. In an embodiment, the memory 314 may store application programs used to implement aspects of the functionality of the systems and methods described herein. In one embodiment, the memory 314 may store raw data, recorded data, and/or calculated data. In some embodiments, as explained in further detail below, the memory 314 may act as a data storage buffer. The memory 314 may include both read only memory and random access memory, and may further include memory cards or other removable storage devices.

In some embodiments of the present invention, the memory 314 may store raw data, recorded data, and/or calculated data permanently, while in other embodiments the memory 314 may only store all or some data temporarily, such as in a buffer. In one embodiment of the present invention, the memory 314, and/or a buffer related thereto, may store data in memory locations of predetermined size such that only a certain quantity of data may be saved for a particular application of the present invention.

The transceiver 318 depicted in FIG. 15 may enable the smart sport ball 300 to wirelessly communicate with other components of the system, such as the HUD 100 or a mobile phone 2014. In one embodiment, the smart sport ball 300 and the other local components of the system may communicate over a personal area network or local area network using, for example, one or more of the following protocols: ANT, ANT+ by Dynastream Innovations, Bluetooth, Bluetooth Low Energy Technology, BlueRobin, or suitable wireless personal or local area network protocols. Other known communication protocols suitable for an motion monitoring system 100 may also be used.

In one embodiment, the 318 is a low-power transceiver. In some embodiments, the transceiver 318 may be a two-way communication transceiver 318, while in other embodiments the transceiver 318 may be a one-way transmitter or a one-way receiver.

The acceleration sensor 316 may be adapted to measure the acceleration of the smart sport ball 300, including the acceleration due to the Earth's gravitational field. In one embodiment, the acceleration sensor 316 may include a tri-axial accelerometer that is capable of measuring acceleration in three orthogonal directions. In other embodiments one, two, three, or more separate accelerometers may be used.

It is possible to use smart soccer balls 300, such as those described above, to obtain ball speed, ball spin rate, ball spin axis, and ball launch angle data using experimental methods. Based on the data obtained, given a suitably large and representative sample and suitably precise measurement techniques, and assuming the energy transfer between the foot 12 and smart soccer ball 300 depends solely on the inertial and elastic properties of smart soccer ball 300 (which are constant), it is also possible to undertake a multi-variable regression analysis to link ball speed, ball spin rate, ball spin axis, and ball launch angle data to points of impact location data for a smart soccer balls 300. This process is described in detail in commonly owned U.S. patent application Ser. No. 14/120,272, filed May 14, 2014.

Figure 16:
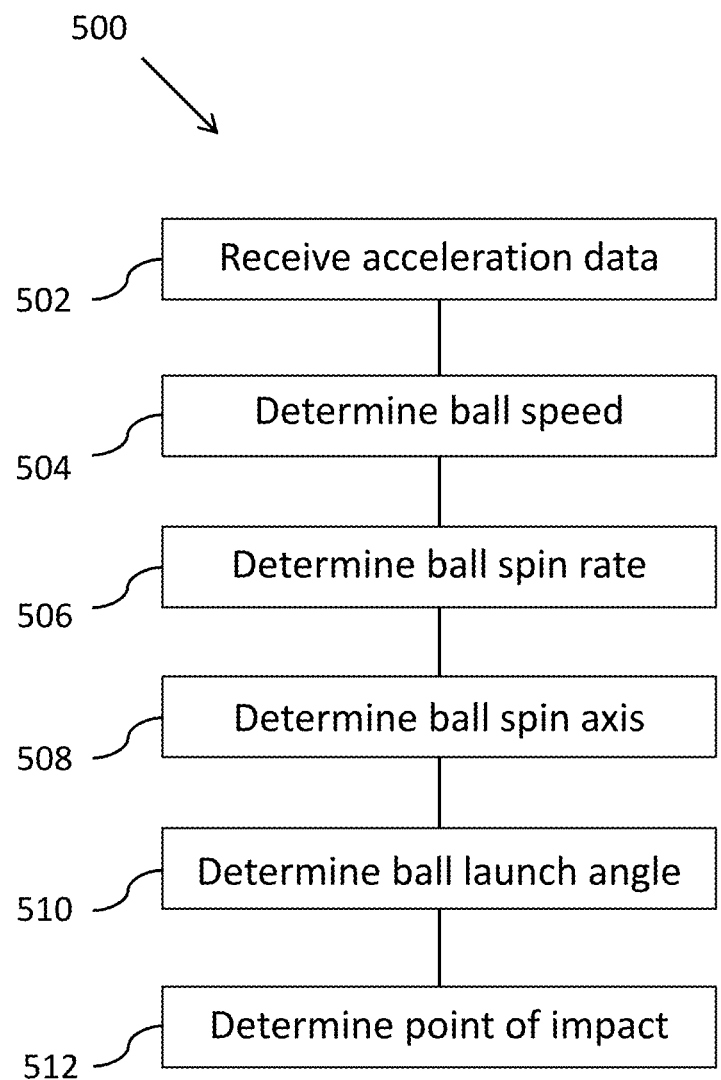
FIG. 16 is a flow chart illustrating a sport ball metric determination process according to an embodiment of the present invention.

In sum, as illustrated in FIG. 16, a regression analysis process 500 begins at step 502 by receiving acceleration data. At step 504, the regression analysis determines soccer ball 20 speed. At step 506, the regression analysis determines soccer ball 20 spin rate. At step 508, the regression analysis determines soccer ball 20 spin axis. At step 510, the regression analysis determines soccer ball 20 launch angle. Each of these parameter determining steps may be conducted in accordance with the discussion provided in commonly owned U.S. patent application Ser. No. 14/120,272, filed May 14, 2014. Finally, at step 512, the regression analysis determines the location of a point of impact on the soccer ball 20.

Figure 17:
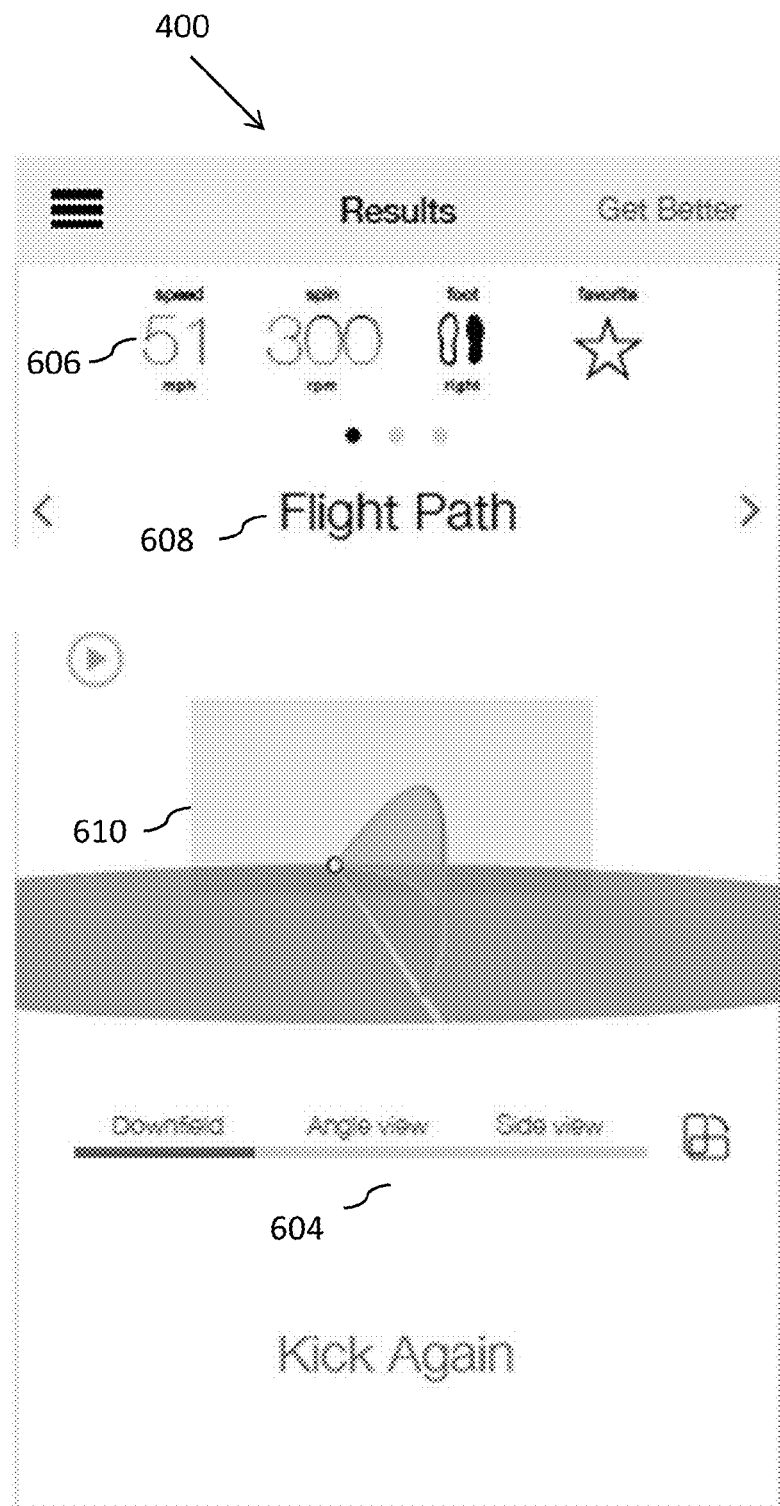
FIG. 17 is an illustration of a HUD projected image field according to an embodiment of the present invention.

FIG. 17 is an illustration of a HUD 100 projected image field 400 display according to an embodiment of the present invention that relies on data obtained from a smart soccer ball 300. This projected image field 400 display provides a visual display to the individual 10 giving them feedback about the motion characteristics of the smart soccer ball 300 during their kick. The exemplary projected image field 400 display includes a statistical display bar 606 that may provide, for example, information on the maximum speed of the smart soccer ball 300 during the post-kick flight or information on the maximum spin rate of the smart soccer ball 300 during the post-kick flight. In some embodiments, the statistical display bar 606 may also provide an indication of which foot 12 the individual 10 kicked the smart soccer ball 300 with, as well as an indication of whether the individual 10 has designated the kick as a "favorite" kick.

The exemplary projected image field 400 display of FIG. 17 also includes a video element 610. The exemplary video element 610 shown is an animation that represents the flight path of the smart soccer ball 300 in three dimension, set upon the background of a representation of a soccer goal 30. In some embodiments the animation may start automatically, while in other embodiments the individual 10 must provide an input to the HUD 100 to request that the video play. In one embodiment, the perspective of the animated flight path may change such that the individual's 10 perspective may appear to rotate around the animated flight path to provide a better perspective on the flight path. In another embodiment the individual 10 may be presented with a selection icon 604 allowing the individual 10 to choose different animated views of the kick and fight path such as, for example, a downfield view, an angled view, or a side view. The particular flight path shown and animated may be based partially or entirely on the determined motion characteristics of the smart soccer ball 300, such that the flight animated flight path is a realistic approximation of the actual flight path of the kicked smart soccer ball 300.

Other visual displays giving feedback about the motion characteristics of the smart soccer ball 300 during their kick may also be provided to the individual 10. In one embodiment, as shown in FIG. 17, a swipe element 608 may indicate to the individual 10 that swiping their finger across a suitable user input portion of the HUD 100 may lead to other views that display additional feedback.

Figure 18:
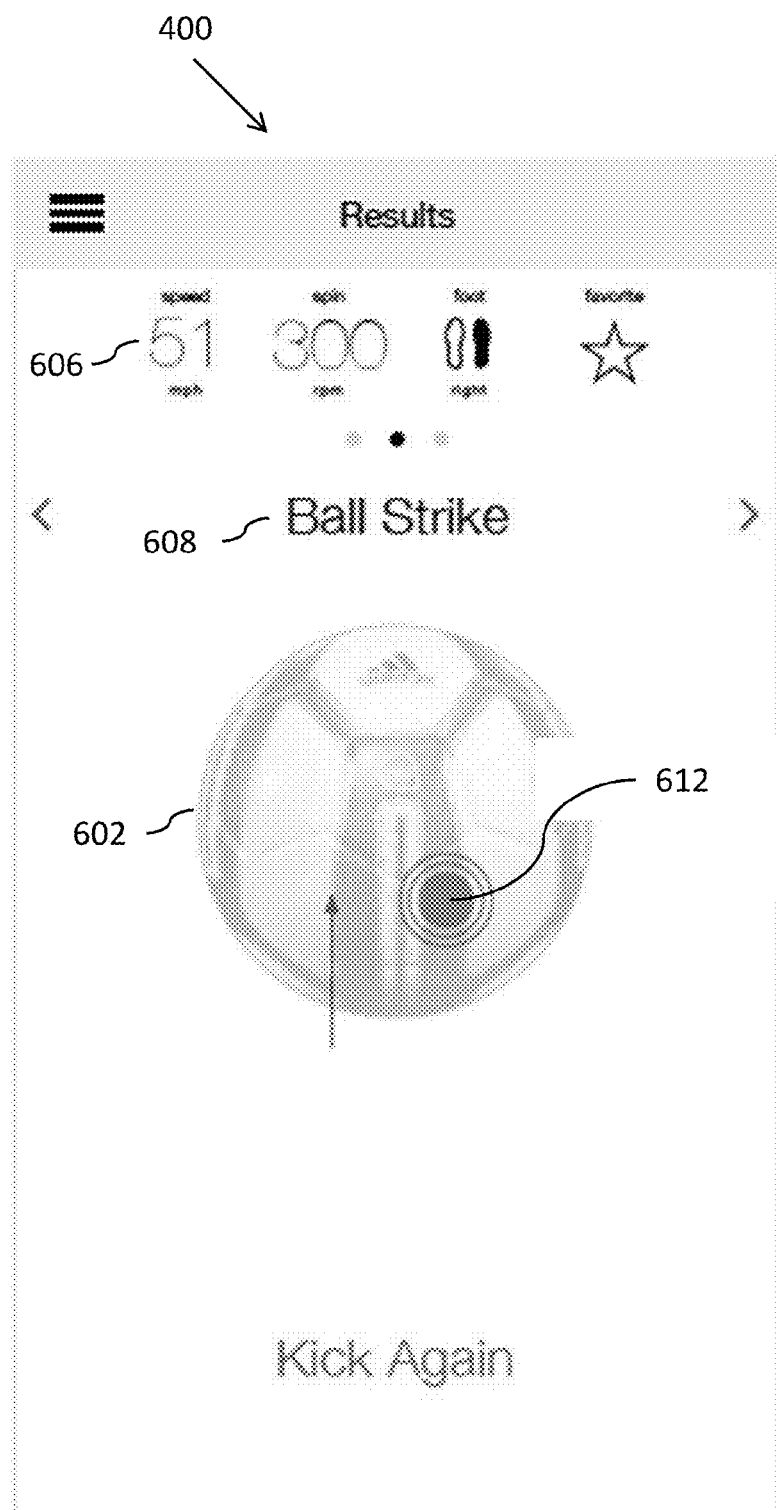
FIG. 18 is an illustration of a HUD projected image field according to an embodiment of the present invention.

FIG. 18 is an illustration of another HUD 100 projected image field 400 display according to an embodiment of the present invention. This projected image field 400 display provides a ball strike display. For example, the exemplary projected image field 400 display of FIG. 18 could be displayed to the individual 10 after the individual 10 swiped their finger across a suitable user input portion of the HUD 100 to transition from the display of flight path feedback of FIG. 17 to the display of FIG. 18.

FIG. 18 provides information on point of impact data. Such data may be obtained, for example, according to a regression process 500 analysis as described above with respect to FIG. 16. As noted above, a relationship exists between the location of the point of impact between an individual's 10 foot 12 and a smart soccer ball 300 and motion characteristics of the smart soccer ball 300 during and after it is kicked. The exemplary projected image field 400 display of FIG. 18 illustrates a point of impact icon 612 overlaid on top of a ball icon 602, where the point of impact icon 612 is representative of the calculated point of impact derived from the regression process 500 analysis as described above with respect to FIG. 16. In other words, the point of impact icon 612 displayed via HUD 100 corresponds to the calculated point of impact that represents the location on the surface of the smart soccer ball 300 that approximately coincides with the center of the area of the foot 12 in contact with the smart soccer ball 300.

Accordingly, the methods previously described for analyzing the relationship between the location of the point of impact between an individual's 10 foot 12 and a smart soccer ball 300 and motion characteristics of the smart soccer ball 300 during and after it is kicked can be used to generate feedback to the individual 10 via the HUD 100, such as visually illustrating the location of a point of impact icon 612 overlaid on top of a ball icon 602, as shown in FIG. 18. The point of impact icon 612 shown in FIG. 18 includes a circular dot with a series of animated rings that may visually "pulse" to help draw attention to the location of the point of impact icon 612. This particular point of impact icon 612 appears below and to the right of the center of the smart soccer ball 300, as viewed from a front perspective.

In another embodiment, the HUD 100 may be capable of determining the location of the smart soccer ball 300 within the projected image field 400 and may visually display the point of impact icon 612 overlaid on top of the individual's 10 actual view of the smart soccer ball 300 falling within the projected image field 400, as opposed to overlaid on top of a ball icon 602. The location of the smart soccer ball 300 within the projected image field 400 may be determined, for example, using the video camera 118 of the HUD 100 and or by receiving data from the smart soccer ball 300 indicative of its location.

The exemplary projected image field 400 display of FIG. 18 also includes the same statistical display bar 606 shown in FIG. 17 that provides information on the maximum speed of the smart soccer ball 300 during the post-kick flight, information on the maximum spin rate of the smart soccer ball 300 during the post-kick flight, an indication of which foot 12 the individual 10 kicked the smart soccer ball 300 with, as well as an indication of whether the individual 10 has designated the kick as a "favorite" kick. The exemplary projected image field 400 display of FIG. 18 additionally includes the same swipe element 608 shown in FIG. 17 that may indicate to the individual 10 that swiping their finger across a suitable user input portion of the HUD 100 may lead to other views that display additional feedback.

Figure 19:
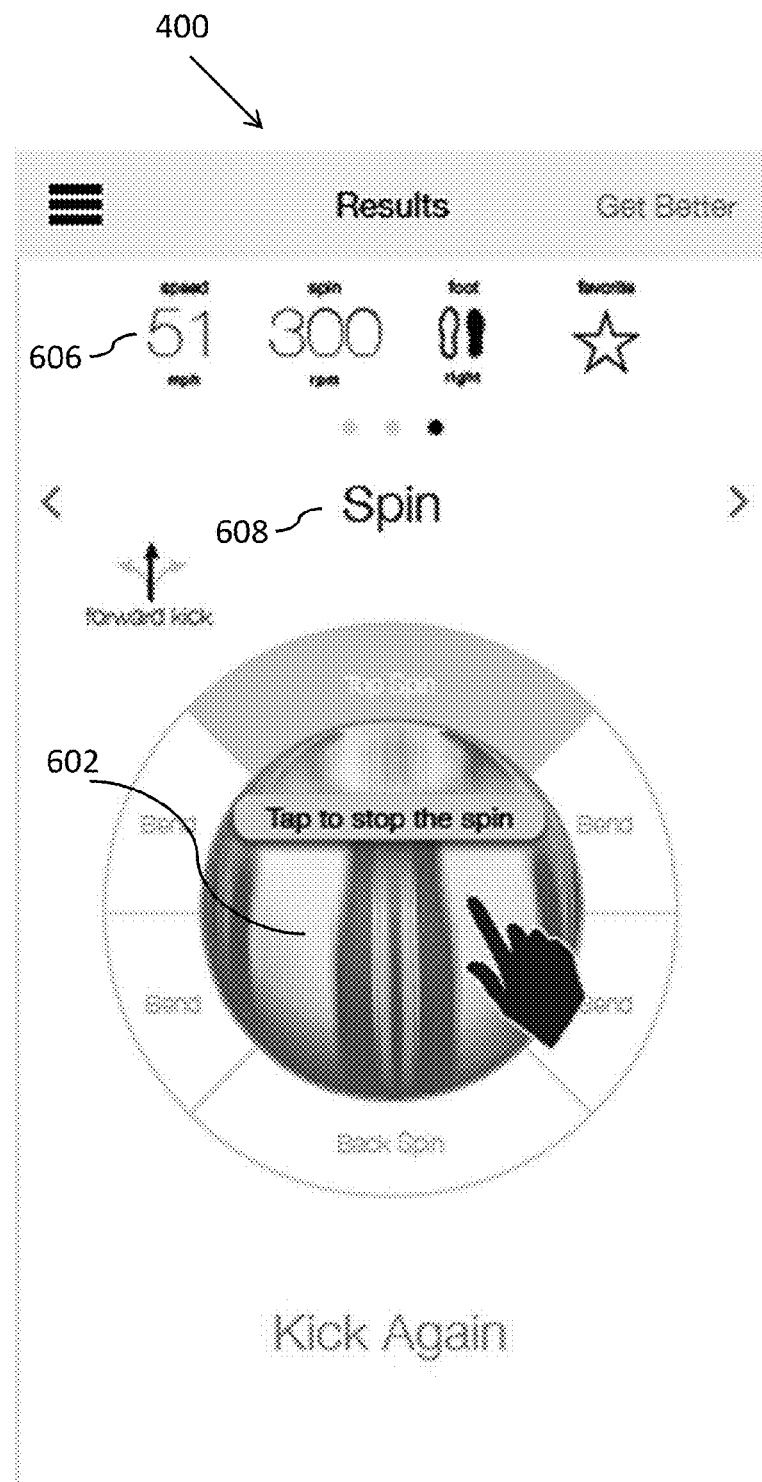
FIG. 19 is an illustration of a HUD projected image field according to an embodiment of the present invention.

FIG. 19 is an illustration of yet another HUD 100 projected image field 400 display according to an embodiment of the present invention. This projected image field 400 display provides a spin display. For example, the exemplary projected image field 400 display of FIG. 19 could be displayed to the individual 10 after the individual 10 swiped their finger across a suitable user input portion of the HUD 100 to transition from the display of flight path feedback of FIG. 18 to the display of FIG. 19.

FIG. 19 provides information on ball spin data. Such data may be obtained, for example, according to analysis as described above with respect to FIG. 16 using a smart soccer ball 300. The exemplary projected image field 400 display of FIG. 19 also includes the same statistical display bar 606 shown in FIG. 18 and other figures that provides information on the maximum speed of the smart soccer ball 300 during the post-kick flight, information on the maximum spin rate of the smart soccer ball 300 during the post-kick flight, an indication of which foot 12 the individual 10 kicked the smart soccer ball 300 with, as well as an indication of whether the individual 10 has designated the kick as a "favorite" kick. The exemplary projected image field 400 display of FIG. 19 additionally includes the same swipe element 608 shown in FIG. 18 and other figures that may indicate to the individual 10 that swiping their finger across a suitable user input portion of the HUD 100 may lead to other views that display additional feedback.

The exemplary projected image field 400 display of FIG. 19 features a ball icon 602. In one embodiment, this ball icon 602 may be animated or otherwise depicted to represent the actual spin rate and spin axis of the smart soccer ball 300 during flight. For example, the ball icon 602 illustrated in FIG. 19 appears to be spinning rapidly with topspin. In embodiments of the present invention, the ball icon 602 may depict ball spin by way of animation, by way of a stationary image with indicia (e.g. arrows) to indicate a direction of spin, or by simply providing a numerical spin rate value, such as three hundred revolutions per minute. In some embodiments, as depicted in FIG. 19, the ball icon 602 may include a ringed border demarcating various zones such as topspin, backspin, or various "bend" zones. The bend zones may correspond to kicks that have sidespin alone or some degree of sidespin coupled with topspin or backspin.

In one embodiment of the preset invention, the visually depicted spin rate of an animated spinning ball icon 602 may be equal to the calculated spin rate of the smart soccer ball 300. For example, if the calculated spin rate of the smart soccer ball 300 is three hundred revolutions per minute, the visually depicted spin rate of an animated spinning ball icon 602 may three hundred revolutions per minute. In another embodiment of the present invention, the visually depicted spin rate of an animated spinning ball icon 602 may be proportional to, but not equal to, the calculated spin rate of the smart soccer ball 300. For example, if the calculated spin rate of the smart soccer ball 300 is three hundred revolutions per minute, the visually depicted spin rate of an animated spinning ball icon 602 may half of that spin rate—or one hundred and fifty revolutions per minute. In still other embodiments, the visually depicted spin rate of an animated spinning ball icon 602 may not be correlated to the calculated spin rate of the smart soccer ball 300.

In another embodiment, the HUD 100 may be capable of determining the location of the smart soccer ball 300 within the projected image field 400 and may visually display the spinning ball icon 602 overlaid on top of the individual's 10 actual view of the smart soccer ball 300 falling within the projected image field 400, as opposed to overlaid on top of a ball icon 602.

In this way, the ball flight path, ball strike, and ball spin visual display and feedback features illustrated in FIGS. 17-19 can provide an individual 10 with useful and visually interesting feedback on the motion characteristics of their kicks of a smart soccer ball 300. As previously noted, in some embodiments, the statistical display bar 606 may provide an indication of whether the individual 10 has designated a particular kick as a "favorite" kick. The individual 10 may designate a kick as a favorite kick after reviewing their feedback while viewing a display such as those of FIGS. 17-19 by providing a user input to the HUD 100. The athletic activity monitoring HUD 100 system will then save a record of the kick being a favorite kick of the individual 10 in a memory device of the HUD 100.

Embodiments of the present invention employing a HUD 100 in combination with a smart soccer ball 300 may provide additional benefits to the individual 10. For example, the locations of target icons 402, flight path icons 406, strike zone icons 414, point of impact icons 416, and footstep icons 418 that are displayed in the projected image field 400 may be determined, in whole or in part, based on data received from the smart soccer ball 300. In addition, parameters such as the individual's step count, approach speed, body alignment, and form described above as being calculated based on data from the HUD 100, a mobile phone 2014, and/or the body-mounted device 206 may further be based, in whole or in part, on data received from the smart soccer ball 300. For example, sensors in the smart soccer ball 300 may be used to sense vibrations associate with the individual taking steps toward the smart soccer ball 300 and eventually kicking the smart soccer ball 300.

Moreover, embodiments of the present invention employing a HUD 100 having a video camera 118 in combination with a smart soccer ball 300 may be able to determine the orientation of the smart soccer ball 300 to the goal 30—i.e. determine when a goal is scored based on a recorded video image of the smart soccer ball 300 entering the goal 30 and data from the smart soccer ball 300 based on the time of impact or other relevant data.

Embodiments of the present invention employing a HUD 100 having a microphone 120 in combination with a smart soccer ball 300 may be able to determine the number of smart soccer ball 300 touches or to determine how "clean" a kick was based on the sound profile as recorded by the microphone 120 and based on data from the smart soccer ball 300 based on the time of impact or other relevant data.

Embodiments of the present invention employing a HUD 100 in combination with a smart soccer ball 300 may further be able to determine which player among a group of players (e.g. members of a team) kicked the smart soccer ball 300 to the extent that the system may pair RFID (or similar ID technologies) data or other data associated with each individual 10 to each impact of the smart soccer ball 300.

Figure 20:
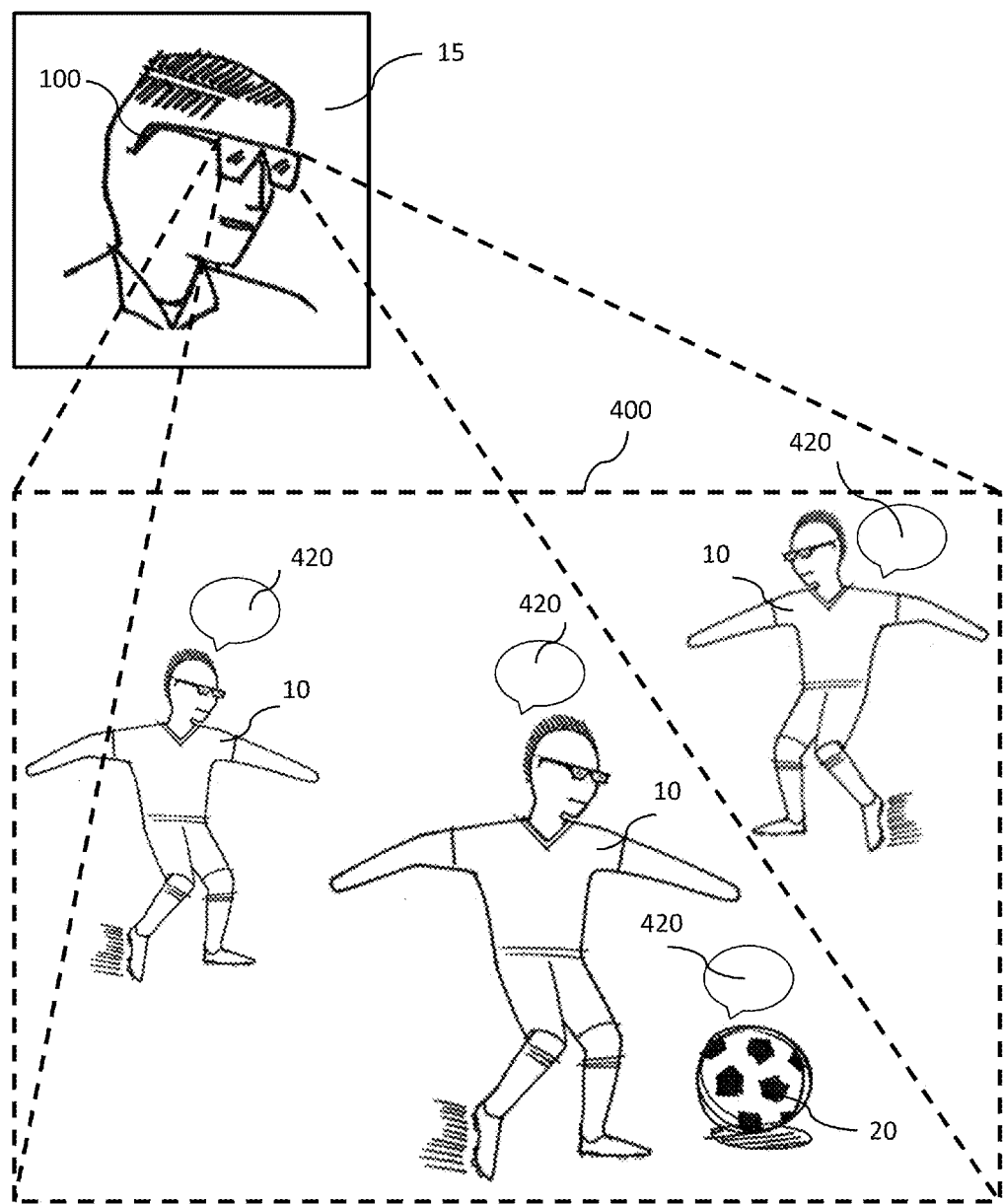
FIG. 20 is an illustration of an interested observer using a HUD to view a plurality of individuals engaged in an athletic activity according to an embodiment of the present invention.

FIG. 20 is an illustration of an interested observer using a HUD 100 to view a plurality of individuals 10 engaged in an athletic activity according to an embodiment of the present invention. Specifically, FIG. 20 depicts a coach 15 equipped with a HUD 100 taking the form of a pair of glasses observing multiple individuals 10 engaged in a game of soccer, all of whom fall within the projected image field 400 of the coach's 15 HUD 100. The coach's 15 HUD 100 may operate similarly to the HUDs 100 described throughout this specification. Exemplary coach 15 devices 210 and related systems having certain athletic performance monitoring features that may be advantageously used in concert with the athletic activity HUD 100 systems and methods of the present invention are disclosed in commonly owned U.S. patent application Ser. No. 13/543,428, filed Jul. 6, 2012 (which published as U.S. Patent App. Pub. No. 2013-0041590).

In one embodiment of the present invention, the coach's 15 HUD 100 may present the coach 15 with informational icons 420 for items of interest falling within the coach's 15 projected image field 400. For example, as illustrated in FIG. 20, three different individuals 10 and a soccer ball 20 falling within the coach's 15 projected image field 400 may be annotated with informational icons 420 that could present information identifying these objects or providing other relevant athletic performance data or relevant player information about them. For example, informational icons 420 may provide the coach 15 with information on player pass completion rate, distance traveled, and fouls.

In another embodiment of the present invention, the coach's 15 HUD 100 may allow the coach 15 to communicate with one or more individuals 10 during an activity, such as players also equipped with HUDs 100. Communication may include audio (e.g. voice) communication and/or visual (e.g. text messages, images, or videos) communication. In one embodiment, the coach's 15 HUD 100 may present the coach 15 with a visual illustration of a desired play, formation, player route, or other visual information about desired player movement during the activity. And in some embodiments, the system could be adapted such that one or more players (e.g. all players, a team captain, or a player currently in possession of the ball 20) can simultaneously view the same visual information about desired player movement on their own HUD 100 that the coach 15 is viewing in his HUD 100. In this way, a coach 15 and his players can share information and strategize in real time during an athletic activity about desired player movements without having to huddle together during a stoppage of play (e.g. a timeout).

In one embodiment of the present invention, individuals 10 each having HUDs 100 playing over a wireless network could play networked games similar to how video games have evolved to enable remote play. For example, a virtual penalty kick mode could be enabled where an individual 10 in one location lines up to take a shot on goal while an individual 10 in another location lines up to block the shot. The first individual 10 would see a virtual representation of the other individual 10 that responds to that individual's 10 motion in their projected image field 400. The second individual 10 would see a virtual representation of the first individual 10 as well as virtual representation of a ball in their projected image field 400. In this example, both individuals 10 would be able to react to the others motions and the second individual 10 would be forced to react to the virtual ball launched at him.

In embodiments of the present invention employing a HUD 100 having a video camera 118 in combination with a smart soccer ball 300 may be able to determine the orientation of the smart soccer ball 300 to the goal 30—i.e. determine when a goal is scored based on a recorded video image of the smart soccer ball 300 entering the goal 30 and data from the smart soccer ball 300 based on the time of impact or other relevant data. The system may further be able to determine which player is in control of the ball or which player most recently kicked the ball based on recorded video data of the game play and data from the smart soccer ball 300 based on the time of impact or other relevant data. In one embodiment, the coach's 15 HUD may store data associated with individual players in association with a profile for that player for later analysis or sharing with the player.

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments of the monitoring system described with reference to the figures will so fully reveal the general nature of the invention that others can, by applying knowledge within the skill of the art, readily modify and/or adapt for various applications such specific embodiments, without undue experimentation, without departing from the general concept of the present invention.

While various embodiments of the present invention have been described above, they have been presented by way of example only, and not limitation. It should be apparent that adaptations and modifications are intended to be within the meaning and range of equivalents of the disclosed embodiments, based on the teaching and guidance presented herein. It therefore will be apparent to one skilled in the art that various changes in form and detail can be made to the embodiments disclosed herein without departing from the spirit and scope of the present invention. The elements of the embodiments presented above are not necessarily mutually exclusive, but may be interchanged to meet various needs as would be appreciated by one of skill in the art.

It is to be understood that the phraseology or terminology used herein is for the purpose of description and not of limitation. The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

What is claimed is:

1. A method of using an athletic activity heads up display system during an athletic activity, comprising:
   a heads up display unit optically recognizing the presence of a sport ball in the heads up display unit's projected image field; and
   the heads up display unit displaying an image to an individual overlaid on the individual's present field of view of an environment,
      wherein the displayed image indicates an objective for the individual,
      wherein the objective is for the individual to approach the sport ball on foot in a specific manner,
      wherein the displayed image indicates the specific manner by which the individual should approach the sport ball on foot, and
      wherein the specific manner comprises one of a desired speed, timing, and cadence of footsteps.

2. The method of claim 1, wherein the displayed image is overlaid on the sport ball falling in the display unit's projected image field.

3. The method of claim 2, wherein the objective is for the individual to strike a specific location on the sport ball, and wherein the displayed image indicates the specific location on the sport ball where the individual should attempt to strike.

4. The method of claim 2, wherein the objective is for the individual to direct the sport ball into a specific location in the goal area, and wherein the displayed image indicates the specific location in the goal area.

5. The method of claim 1, wherein the location of the displayed image is varied over time throughout the display unit's projected image field.

6. The method of claim 1, wherein the objective is for the individual to direct the sport ball with a specific projected flight path, and wherein the displayed image indicates the specific flight path.

7. The method of claim 6, wherein the specific projected flight path is not constructed from data representing a previous flight path that the individual previously directed the sport ball through.

8. The method of claim 1, wherein the objective is for the individual to direct the sport ball past a virtual defender, and wherein the displayed image represents the virtual defender.

9. The method of claim 1, wherein the heads up display unit optically recognizing the presence of a sport ball comprises the heads up display unit receiving video information providing information about the position of the sport ball, and wherein the video information is used to trigger the taking of a still photo or video clip by the heads up display unit.

* * * * *